(12) United States Patent
Barnes et al.

(10) Patent No.: US 12,426,939 B2
(45) Date of Patent: Sep. 30, 2025

(54) MICRO-INVASIVE SURGICAL DEVICE AND METHODS OF USE

(71) Applicant: Mayo Foundation for Medical Education and Research, Rochester, MN (US)

(72) Inventors: Darryl E. Barnes, Eagan, MN (US); Jay Smith, Byron, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 958 days.

(21) Appl. No.: 17/595,813

(22) PCT Filed: May 29, 2020

(86) PCT No.: PCT/US2020/035094
§ 371 (c)(1),
(2) Date: Nov. 24, 2021

(87) PCT Pub. No.: WO2020/243412
PCT Pub. Date: Dec. 3, 2020

(65) Prior Publication Data
US 2022/0233232 A1    Jul. 28, 2022

Related U.S. Application Data

(63) Continuation of application No. PCT/US2020/012682, filed on Jan. 8, 2020.
(Continued)

(51) Int. Cl.
*A61B 18/14* (2006.01)
*A61B 18/08* (2006.01)
(Continued)

(52) U.S. Cl.
CPC ............ *A61B 18/14* (2013.01); *A61B 18/082* (2013.01); *A61B 18/20* (2013.01);
(Continued)

(58) Field of Classification Search
CPC .................. A61B 18/14; A61B 18/082; A61B 2018/00202; A61B 2018/00601; A61B 2018/1415
See application file for complete search history.

(56) References Cited

U.S. PATENT DOCUMENTS

| 1,057,867 A | 4/1913 | Meadows |
| 2,123,768 A | 7/1938 | Corsico-Piccolini et al. |

(Continued)

FOREIGN PATENT DOCUMENTS

| DE | 4444166 A1 | 6/1996 |
| EP | 3278749 A1 | 2/2018 |

(Continued)

OTHER PUBLICATIONS

International Search Report and Written Opinion dated Aug. 4, 2022 for International Application No. PCT/US2022/027039.
(Continued)

*Primary Examiner* — Erin McGrath
(74) *Attorney, Agent, or Firm* — Seager, Tufte & Wickhem LLP

(57) ABSTRACT

The invention provides a tissue cutting device comprising a handle, a first blade, and a second blade. The second blade is coupled to the handle. The second blade is rotatable relative to the first blade such that the second blade is configured to rotate between a first position and a second position. The second blade is in a same plane as the first blade when the second blade is in the first position. The
(Continued)

second blade is rotated into a different plane from the first blade when the second blade is rotated from the first position toward the second position.

5 Claims, 28 Drawing Sheets

Related U.S. Application Data

(60) Provisional application No. 62/853,930, filed on May 29, 2019.

(51) Int. Cl.
 *A61B 18/20* (2006.01)
 *A61B 18/00* (2006.01)
 *A61B 90/00* (2016.01)

(52) U.S. Cl.
 CPC .............. *A61B 2018/00202* (2013.01); *A61B 2018/00601* (2013.01); *A61B 2018/1415* (2013.01); *A61B 2090/037* (2016.02)

(56) References Cited

U.S. PATENT DOCUMENTS

| | | | |
|---|---|---|---|
| 3,435,826 A | 4/1969 | Fogarty |
| 4,962,770 A | 10/1990 | Agee et al. |
| 4,963,147 A | 10/1990 | Agee et al. |
| 4,979,951 A | 12/1990 | Simpson |
| 5,089,000 A | 2/1992 | Agee et al. |
| 5,125,927 A | 6/1992 | Belanger |
| 5,217,007 A | 6/1993 | Ciaglia |
| 5,306,284 A | 4/1994 | Agee et al. |
| 5,325,883 A | 7/1994 | Orr |
| 5,345,927 A | 9/1994 | Bonutti |
| 5,353,812 A | 10/1994 | Chow |
| 5,425,355 A | 6/1995 | Kulick |
| 5,480,408 A | 1/1996 | Chow |
| 5,569,283 A | 10/1996 | Green et al. |
| 5,620,446 A | 4/1997 | McNamara et al. |
| 5,649,946 A | 7/1997 | Bramlet |
| 5,655,545 A | 8/1997 | Johnson et al. |
| 5,690,663 A | 11/1997 | Stephens |
| 5,690,664 A | 11/1997 | Sauer et al. |
| 5,702,417 A | 12/1997 | Hermann |
| 5,707,382 A | 1/1998 | Sierocuk et al. |
| 5,709,697 A | 1/1998 | Ratcliff et al. |
| 5,735,865 A | 4/1998 | Schaumann et al. |
| 5,755,732 A | 5/1998 | Green et al. |
| 5,766,198 A | 6/1998 | Li |
| 5,769,865 A | 6/1998 | Kermode et al. |
| 5,769,895 A | 6/1998 | Ripamonti |
| 5,772,680 A | 6/1998 | Kieturakis et al. |
| 5,779,053 A | 7/1998 | Partika et al. |
| 5,782,850 A | 7/1998 | Ro |
| 5,782,854 A | 7/1998 | Hermann |
| 5,800,449 A | 9/1998 | Wales |
| 5,810,806 A | 9/1998 | Ritchart et al. |
| 5,813,977 A | 9/1998 | Hinchliffe et al. |
| 5,827,311 A | 10/1998 | Berelsman et al. |
| 5,860,997 A | 1/1999 | Bonutti |
| 5,865,728 A | 2/1999 | Moll et al. |
| 5,893,861 A | 4/1999 | Yumoto |
| 5,904,699 A | 5/1999 | Schwemberger et al. |
| 5,908,433 A | 6/1999 | Eager et al. |
| 5,954,739 A | 9/1999 | Bonutti |
| 5,957,944 A | 9/1999 | Khuri et al. |
| 5,968,061 A | 10/1999 | Mirza |
| 6,004,337 A | 12/1999 | Kieturakis et al. |
| 6,007,554 A | 12/1999 | Van Ess |
| 6,012,586 A | 1/2000 | Misra |
| 6,015,421 A | 1/2000 | Echverry et al. |
| 6,017,356 A | 1/2000 | Frederick et al. |
| 6,019,774 A | 2/2000 | Weiss et al. |
| 6,030,402 A | 2/2000 | Thompson et al. |
| 6,080,175 A | 6/2000 | Hogendijk |
| 6,083,177 A | 7/2000 | Kobren et al. |
| 6,106,496 A | 8/2000 | Amnissolle |
| 6,113,617 A | 9/2000 | van der Merwe |
| 6,117,153 A | 9/2000 | Lary et al. |
| 6,168,608 B1 | 1/2001 | Echeverry et al. |
| 6,171,236 B1 | 1/2001 | Bonutti |
| 6,179,852 B1 | 1/2001 | Strickland |
| 6,217,602 B1 | 4/2001 | Redmon |
| 6,258,113 B1 | 7/2001 | Adams et al. |
| 6,264,604 B1 | 7/2001 | Kieturakis et al. |
| 6,346,085 B1 | 2/2002 | Schiffman |
| 6,358,251 B1 | 3/2002 | Mirza |
| 6,361,543 B1 | 3/2002 | Chin et al. |
| 6,402,770 B1 | 6/2002 | Jessen |
| 6,447,529 B2 | 9/2002 | Fogarty et al. |
| 6,451,042 B1 | 9/2002 | Bonutti |
| 6,514,272 B1 | 2/2003 | Kieturakis et al. |
| 6,565,590 B2 | 5/2003 | Kieturakis et al. |
| 6,592,602 B1 | 7/2003 | Pearetree et al. |
| 6,632,234 B2 | 10/2003 | Kieturakis et al. |
| 6,685,717 B1 | 2/2004 | Ilic |
| 6,746,465 B2 | 6/2004 | Diedrich et al. |
| 6,875,183 B2 | 4/2005 | Cervi |
| 6,896,141 B2 | 5/2005 | McMichael et al. |
| 7,001,405 B2 | 2/2006 | Kieturakis et al. |
| 7,037,317 B2 | 5/2006 | Hermann et al. |
| 7,214,236 B2 | 5/2007 | Kieturakis et al. |
| 7,329,253 B2 | 2/2008 | Brounstein et al. |
| 7,331,462 B2 | 2/2008 | Steppe |
| 7,434,687 B2 | 10/2008 | Itou et al. |
| 7,476,235 B2 | 1/2009 | Diederich et al. |
| 7,481,817 B2 | 1/2009 | Sauer |
| 7,504,875 B2 | 3/2009 | Bhushan et al. |
| 7,520,886 B2 | 4/2009 | Surti |
| 7,628,798 B1 | 12/2009 | Welborn |
| 7,708,751 B2 | 5/2010 | Hughes et al. |
| 7,744,617 B2 | 6/2010 | Lunsford et al. |
| 7,780,690 B2 | 8/2010 | Rehnke |
| 7,918,784 B2 | 4/2011 | Wellborn et al. |
| 7,967,137 B2 | 6/2011 | Fulbrook et al. |
| D645,147 S | 9/2011 | Ruf |
| 8,052,710 B2 | 11/2011 | Kambin et al. |
| 8,105,342 B2 | 1/2012 | Onuki et al. |
| 8,147,487 B2 | 4/2012 | Burbank et al. |
| 8,177,064 B2 | 5/2012 | McCormick et al. |
| 8,246,646 B2 | 8/2012 | Kambin |
| 8,252,013 B2 | 8/2012 | Leibowitz et al. |
| D666,725 S | 9/2012 | McCormack et al. |
| 8,257,379 B2 | 9/2012 | Lee |
| 8,273,098 B2 | 9/2012 | Strickland |
| 8,282,665 B2 | 10/2012 | Kieturakis et al. |
| 8,323,278 B2 | 12/2012 | Brecheen et al. |
| D673,683 S | 1/2013 | McCormack et al. |
| D674,489 S | 1/2013 | McCormack et al. |
| 8,348,966 B2 | 1/2013 | McCormack et al. |
| 8,419,728 B2 | 4/2013 | Klotz et al. |
| 8,449,478 B2 | 5/2013 | Lee et al. |
| 8,500,770 B2 | 8/2013 | Echevery et al. |
| 8,523,891 B2 | 9/2013 | Welborn |
| 8,579,930 B2 | 11/2013 | Palmer et al. |
| 8,603,124 B1 | 12/2013 | Hatch |
| 8,603,738 B2 | 12/2013 | Condeelis et al. |
| 8,608,738 B2 | 12/2013 | Brecheen et al. |
| 8,608,763 B1 | 12/2013 | Jurbala |
| 8,613,745 B2 | 12/2013 | Bleich |
| 8,652,157 B2 | 2/2014 | McCormack et al. |
| 8,672,960 B2 | 3/2014 | Briganti et al. |
| 8,702,654 B2 | 4/2014 | Agee et al. |
| 8,721,668 B2 | 5/2014 | McCormack et al. |
| 8,746,452 B2 | 6/2014 | Tomes et al. |
| 8,753,364 B2 | 6/2014 | McCormack et al. |
| 8,876,845 B2 | 11/2014 | Suddaby |
| 8,906,040 B2 | 12/2014 | Filipi et al. |
| 8,911,470 B2 | 12/2014 | Mirza et al. |
| 8,951,273 B1 | 2/2015 | Fard |
| 8,992,424 B2 | 3/2015 | Orbay et al. |
| 9,017,354 B2 | 4/2015 | Fink et al. |

(56) References Cited

U.S. PATENT DOCUMENTS

| | | | |
|---|---|---|---|
| 9,028,516 B2 | 5/2015 | Palmer et al. |
| 9,050,004 B2 | 6/2015 | Diao et al. |
| D735,330 S | 7/2015 | Rydberg et al. |
| D735,332 S | 7/2015 | Allen et al. |
| 9,113,953 B2 | 8/2015 | Smith |
| 9,131,951 B2 | 9/2015 | Mirza et al. |
| 9,168,057 B2 | 10/2015 | Poulsen |
| 9,186,217 B2 | 11/2015 | Goyal |
| D745,675 S | 12/2015 | Jankwoski et al. |
| 9,532,847 B2 | 1/2017 | Hendrickson et al. |
| 10,206,703 B2 | 2/2019 | Palmer et al. |
| 10,245,062 B2 | 4/2019 | Seymour |
| 10,383,609 B2 | 8/2019 | Nakanishi et al. |
| 10,413,313 B2 | 9/2019 | Brown et al. |
| D864,388 S | 10/2019 | Barber |
| 10,918,410 B2 | 2/2021 | Mirza et al. |
| 11,006,970 B2 | 5/2021 | Mirza et al. |
| 11,096,710 B2 | 8/2021 | Mirza et al. |
| 11,096,720 B2 | 8/2021 | Mirza et al. |
| 11,259,837 B2 | 3/2022 | Aklog et al. |
| D969,316 S | 11/2022 | Milhous et al. |
| D974,561 S | 1/2023 | Walsh |
| 2002/0120211 A1 | 8/2002 | Wardle et al. |
| 2002/0161387 A1 | 10/2002 | Blanco |
| 2002/0185406 A1 | 12/2002 | Massengale et al. |
| 2004/0143280 A1 | 7/2004 | Suddaby |
| 2004/0195131 A1 | 10/2004 | Spolidoro |
| 2005/0209624 A1 | 9/2005 | Vijay |
| 2005/0222598 A1 | 10/2005 | Ho et al. |
| 2005/0228426 A1 | 10/2005 | Campbell |
| 2006/0149136 A1 | 7/2006 | Seto et al. |
| 2006/0190021 A1 | 8/2006 | Hausman et al. |
| 2007/0083225 A1 | 4/2007 | Kiser et al. |
| 2007/0112366 A1 | 5/2007 | Welborn et al. |
| 2007/0118170 A1 | 5/2007 | Kieturakis et al. |
| 2007/0225740 A1 | 9/2007 | Suddaby |
| 2008/0033466 A1 | 2/2008 | Assell et al. |
| 2008/0058588 A1 | 3/2008 | Emanuel |
| 2008/0058846 A1 | 3/2008 | Vosough |
| 2008/0109021 A1 | 5/2008 | Medoff |
| 2008/0195128 A1 | 8/2008 | Orbay et al. |
| 2008/0234713 A1 | 9/2008 | Bernardini |
| 2008/0288041 A1 | 11/2008 | Holman et al. |
| 2009/0048620 A1 | 2/2009 | Weiss et al. |
| 2009/0048623 A1 | 2/2009 | Lafosse et al. |
| 2009/0125044 A1 | 5/2009 | Lary |
| 2009/0171157 A1 | 7/2009 | Diederich et al. |
| 2009/0312740 A1 | 12/2009 | Kim et al. |
| 2009/0312807 A1 | 12/2009 | Boudreault et al. |
| 2010/0010530 A1 | 1/2010 | Rhee |
| 2010/0100114 A1 | 4/2010 | Berger |
| 2010/0125266 A1 | 5/2010 | Deem et al. |
| 2010/0185222 A1 | 7/2010 | Keller |
| 2010/0211082 A1 | 8/2010 | Sauer |
| 2010/0249719 A1 | 9/2010 | Fojtik |
| 2011/0087258 A1 | 4/2011 | Sluss |
| 2011/0112563 A1 | 5/2011 | To et al. |
| 2011/0118601 A1 | 5/2011 | Barnes |
| 2011/0155599 A1 | 6/2011 | Yakel et al. |
| 2011/0201881 A1 | 8/2011 | Emch |
| 2012/0016398 A1 | 1/2012 | Strickland |
| 2012/0029542 A1 | 2/2012 | Huang |
| 2012/0029543 A1 | 2/2012 | Lee |
| 2012/0083816 A1* | 4/2012 | Hajgato ............. A61B 17/3215 606/170 |
| 2012/0191116 A1 | 7/2012 | Flynn et al. |
| 2012/0198703 A1 | 8/2012 | Ranieri et al. |
| 2012/0203220 A1 | 8/2012 | Brannan et al. |
| 2012/0228355 A1* | 9/2012 | Combrowski ..... A61B 17/0642 227/175.1 |
| 2012/0289987 A1 | 11/2012 | Wilson et al. |
| 2012/0303018 A1 | 11/2012 | Ladtkow et al. |
| 2013/0046323 A1 | 2/2013 | Whitaker |
| 2013/0066149 A1 | 3/2013 | Mirza et al. |
| 2013/0144318 A1 | 6/2013 | Dinis Carmo |
| 2013/0165962 A1 | 6/2013 | Porshinsky et al. |
| 2013/0172895 A1 | 7/2013 | Wallace et al. |
| 2013/0197553 A1 | 8/2013 | Ng et al. |
| 2013/0211201 A1 | 8/2013 | Wongsiri |
| 2013/0289596 A1 | 10/2013 | Guo |
| 2013/0345515 A1 | 12/2013 | Fitzmaurice |
| 2014/0012076 A1 | 1/2014 | Mirza et al. |
| 2014/0031621 A1 | 1/2014 | Liu |
| 2014/0039533 A1 | 2/2014 | Palmer et al. |
| 2014/0054356 A1 | 2/2014 | Hartwick et al. |
| 2014/0066709 A1 | 3/2014 | Mirza et al. |
| 2014/0180282 A1 | 6/2014 | Brecheen et al. |
| 2014/0212456 A1 | 7/2014 | Vazquez-Cintron et al. |
| 2014/0276741 A1 | 9/2014 | McKay |
| 2014/0276790 A1 | 9/2014 | Raybin et al. |
| 2014/0343357 A1 | 11/2014 | Mirza et al. |
| 2014/0371526 A1 | 12/2014 | Mirza et al. |
| 2015/0045822 A1 | 2/2015 | Mirza et al. |
| 2015/0073461 A1 | 3/2015 | McCormack et al. |
| 2015/0080878 A1 | 3/2015 | Feng et al. |
| 2015/0080905 A1 | 3/2015 | Begemann et al. |
| 2015/0133982 A1 | 5/2015 | Park |
| 2015/0182248 A1 | 7/2015 | Palmer et al. |
| 2015/0196743 A1 | 7/2015 | Diederich et al. |
| 2015/0201959 A1 | 7/2015 | Guo |
| 2015/0265818 A1 | 9/2015 | Piskun et al. |
| 2015/0282832 A1 | 10/2015 | Mirza et al. |
| 2015/0320436 A1 | 11/2015 | Agee et al. |
| 2016/0081710 A1 | 3/2016 | Barnes et al. |
| 2016/0157880 A1 | 6/2016 | Aklog et al. |
| 2016/0235431 A1 | 8/2016 | Brown et al. |
| 2017/0042565 A1 | 2/2017 | Ellsworth et al. |
| 2017/0086803 A1 | 3/2017 | Nakanishi et al. |
| 2017/0105792 A1 | 4/2017 | Barnes et al. |
| 2017/0143364 A1 | 5/2017 | Mirza et al. |
| 2018/0200902 A1* | 7/2018 | Yang ................. B26B 21/4012 |
| 2019/0262024 A1 | 8/2019 | Barnes et al. |
| 2019/0343546 A1 | 11/2019 | Brown et al. |
| 2020/0078039 A1 | 3/2020 | Mirza et al. |
| 2020/0107850 A1 | 4/2020 | Mirza et al. |
| 2020/0197039 A1 | 6/2020 | Hatch |
| 2021/0077139 A1 | 3/2021 | Mirza et al. |
| 2021/0369293 A1 | 12/2021 | Moungondo |
| 2022/0022909 A1 | 1/2022 | Lins et al. |
| 2022/0346819 A1 | 11/2022 | Barnes et al. |
| 2022/0354527 A1 | 11/2022 | Barnes |

FOREIGN PATENT DOCUMENTS

| | | |
|---|---|---|
| WO | 2007016141 A2 | 2/2007 |
| WO | 2012089767 A1 | 7/2012 |
| WO | 2013155472 A1 | 10/2013 |
| WO | 2014118752 A2 | 8/2014 |
| WO | 2014176206 A2 | 10/2014 |
| WO | 2014176206 A3 | 1/2015 |
| WO | 2020146458 A1 | 7/2020 |
| WO | 2020243412 A1 | 12/2020 |
| WO | 2020247476 A1 | 12/2020 |

OTHER PUBLICATIONS

Invitation to Pay Additional Fees dated Mar. 31, 2023 for International Application No. PCT/US/2023/011838.

Muramatsu et al., "A Comparison of Blinded Versus Ultrasound-Guided Limited-Open Trigger Finger Release using the Yasunaga Knife," Journal of Hand Surgery, Asian Pacific, vol. 27, No. 1 pp. 124-129, Feb. 2022.

S2S Surgical™ Surgeon-2-Surgeon Innovation , Trigger Finger Release Surgial Technique, Version 1.1, 5 pages, www.S2Surgical.com 2017.

International Search Report and Written Opinion issued Sep. 21, 2020, in International Application No. PCT/US20/35094.

U.S. Appl. No. 62/086,950, filed Dec. 3, 2014 (52 pages).

International Search Report and Written Opinion mailed Feb. 15, 2016, issued in International Application No. PCT/US2015/049558 (24 pages).

(56) References Cited

OTHER PUBLICATIONS

Examination Report issued in European Patent Application No. 15767038.1, dated Apr. 29, 2019 (8 pages).
International Search Report and Written Opinion mailed Mar. 25, 2022, in Application No. PCT/US22/70088.
Extended European Search Report for Application No. 20738258.1 dated Feb. 23, 2022.
International Search Report and Written Opinion mailed Jun. 15, 2020, in Application No. PCT/US20/12682.

* cited by examiner

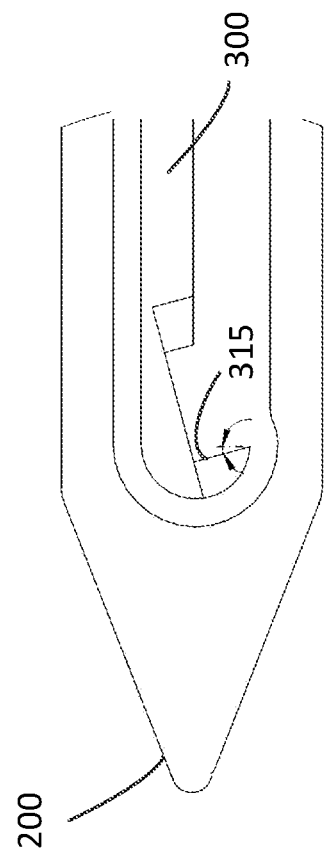
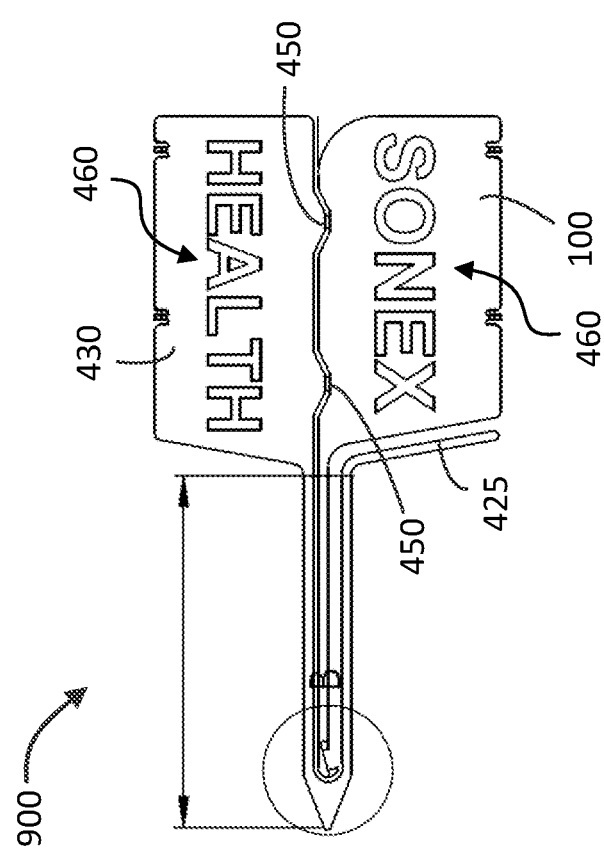
FIG. 23B
FIG. 23A

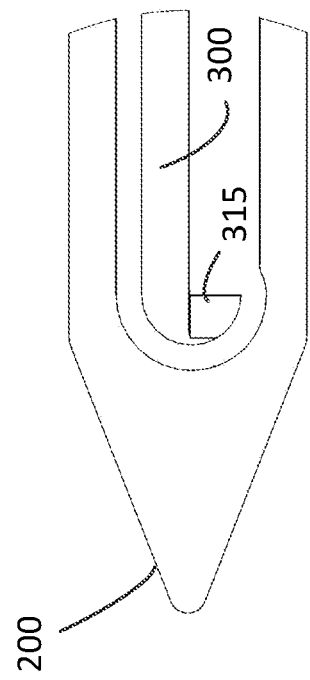
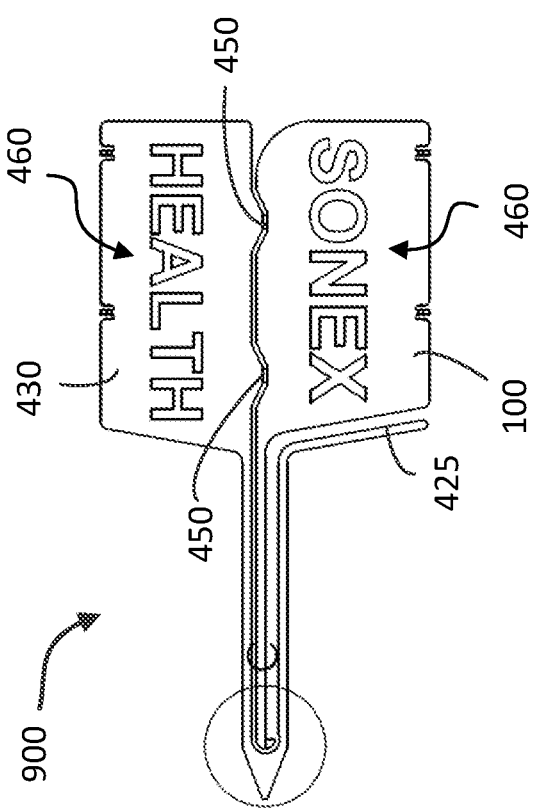

MICRO-INVASIVE SURGICAL DEVICE AND METHODS OF USE

RELATED APPLICATION APPLICATIONS

This application is a U.S. national phase application under 35 U.S.C. § 371 of International Patent Application No. PCT/US2020/035094, which claims priority to International Patent Application No. PCT/US2020/012682 filed Jan. 8, 2020, which in turn claims priority to U.S. Provisional Application No. 62/853,930, filed May 29, 2019, and International Patent Application No. PCT/US2020/035094 also claims priority to U.S. Provisional Patent Application No. 62/853,930, filed May 29, 2019, disclosures of which are incorporated herein by reference in their entireties.

FIELD OF THE INVENTION

The present invention relates generally to a micro-invasive surgical device. More specifically, the present invention relates to a micro-invasive tissue cutting device having a first blade and a second blade, wherein the second blade is rotatable relative to the first blade. The present invention also provides methods of using the tissue cutting device, including a method of treating trigger finger.

BACKGROUND OF THE INVENTION

The first annular ("A1") pulley is a small band of tissue on the palmar side of a person's hand. In some cases, the flexor tendon thickens and a nodule can get caught on the A1 pulley and cause irritation. The flexor tendon can then become locked in place when a person flexes his or her fingers. This condition is commonly referred to as "trigger finger." To treat trigger finger, the A1 pulley is typically cut so as to release the tendon. For this purpose, certain devices are known that use a hook blade to perform such a procedure. However, a hook blade tends to slide off the tendon. Moreover, with such conventional devices, an additional, separate device is often required to introduce the hook blade into the person's skin.

As set forth in the present disclosure, it would be desirable to provide a tissue cutting device having a first blade and a second blade, wherein the second blade is rotatable relative to the first blade. In some cases, it would be desirable to provide such a device where the first blade facilitates introducing the tissue cutting device into and through a patient's skin. It would also be desirable to provide a device having a second blade that is protected by the first blade until the second blade is deployed for a cutting procedure. Additionally, it would be desirable to provide a tissue cutting device that is minimally invasive and that can be used to treat trigger finger. Still further, it would be desirable to provide a tissue cutting device having a lock for selectively controlling rotation of the second blade relative to the first blade. Further yet, it would be desirable to provide a tissue cutting device having one or more break points between the first blade and the second blade, wherein the one or more break points are configured to be disrupted.

SUMMARY OF THE INVENTION

In some embodiments, the invention provides a tissue cutting device comprising a handle, a first blade, and a second blade. The first blade and the second blade are coupled to the handle. The first blade is an exposed blade. The second blade is rotatable relative to the first blade such that the second blade is configured to rotate between a first position and a second position. The second blade is in a same plane as the first blade when the second blade is in the first position. The second blade is rotated into a different plane from the first blade as the second blade is rotated from the first position toward the second position. The second blade is an unexposed blade when in the first position and is an exposed blade when in the second position.

Certain other embodiments of the invention provide a tissue cutting device comprising a handle, a first blade, and a second blade. The first blade extends away from the handle, and the second blade is coupled to the handle. The second blade is rotatable relative to the first blade such that the second blade is configured to rotate between a first position and a second position. The tissue cutting device further includes a cover that is coupled to the handle. The second blade rotates from the first position toward the second position in response to rotation of the handle relative to the cover.

Certain other embodiments of the invention provide a tissue cutting device comprising a handle, a first blade, a second blade and one or more break points between the first blade and the second blade, the one or more break points being configured to be disrupted. When the one or more break points are intact, the first blade is connected to the second blade. When each of the one or more break points is disrupted, the first blade is separated from the second blade. In some cases, the one or more break points are configured to be disrupted by either rotational force or shear force.

BRIEF DESCRIPTION OF THE DRAWINGS

FIG. 23A is a schematic view of a tissue cutting device having one or more break points in accordance with certain embodiments of the present disclosure.

FIG. 23B is a detailed view of the first and second blades shown in FIG. 23A.

FIG. 24A is a schematic view of a tissue cutting device having one or more break points in accordance with certain embodiments of the present disclosure.

FIG. 24B is a detailed view of the first and second blades shown in FIG. 24A.

DETAILED DESCRIPTION OF PREFERRED EMBODIMENTS

Figure 1:
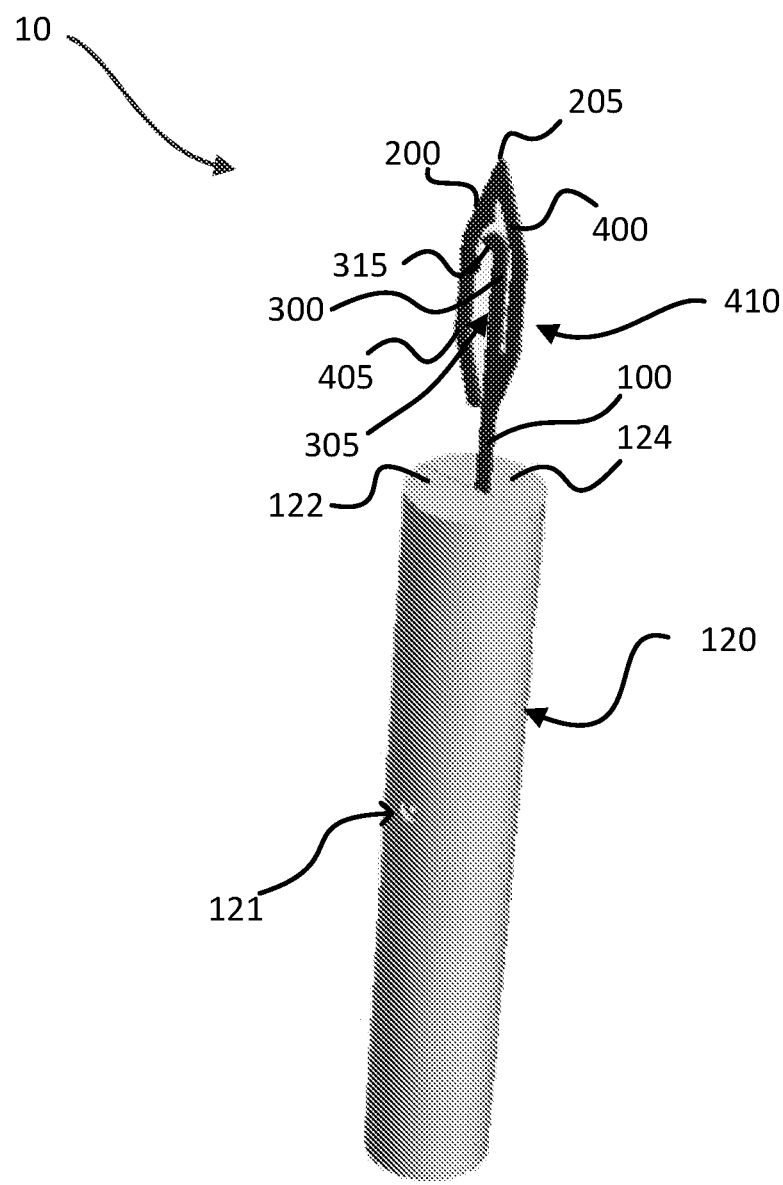
FIG. 1 is a top perspective view of a tissue cutting device in accordance with certain embodiments of the present disclosure, showing a handle coupled to a housing and a second blade in a first (inactive) position.
Figure 2:
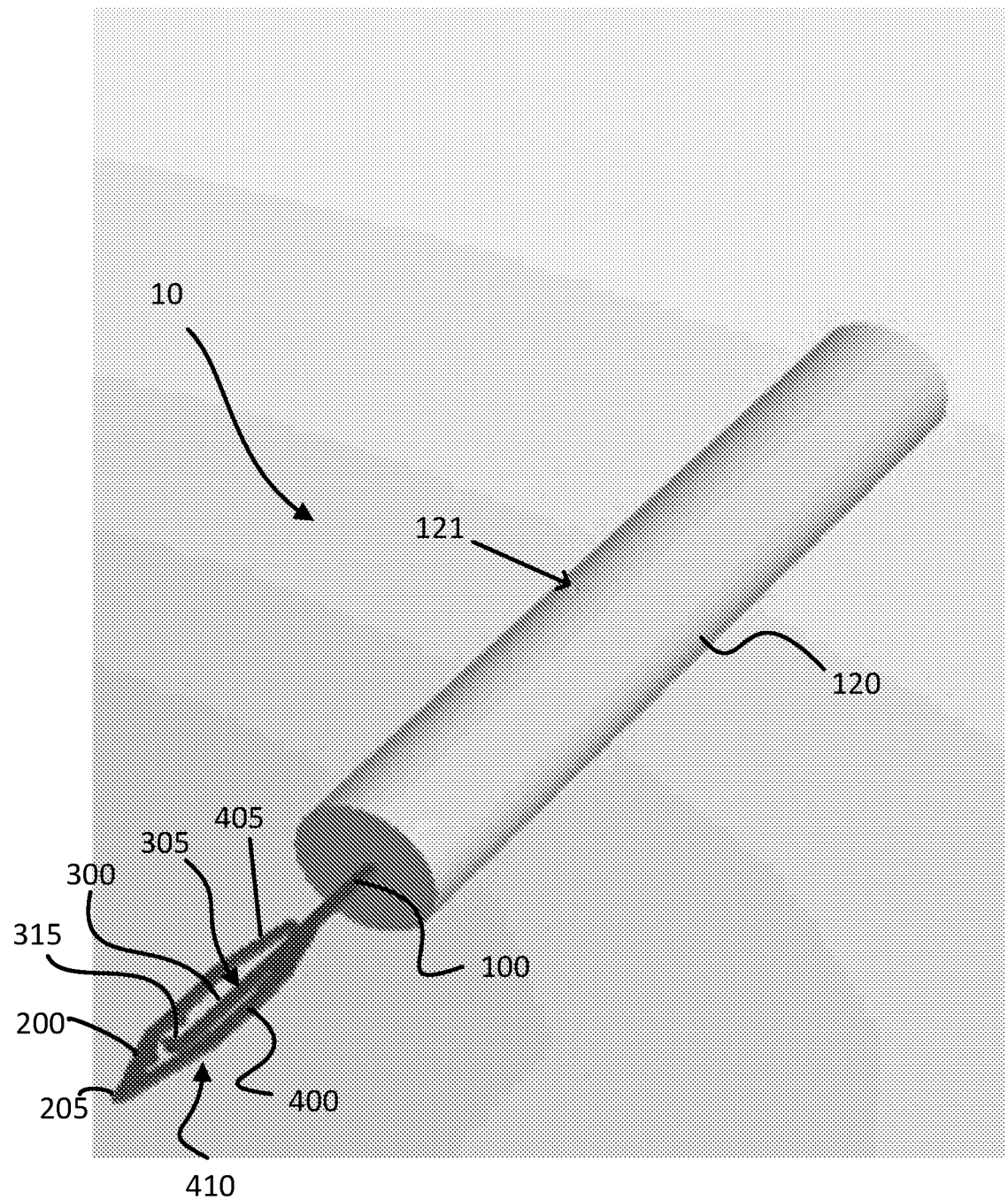
FIG. 2 is another top perspective view of the tissue cutting device of FIG. 1, showing the second blade in the first position.
Figure 3:
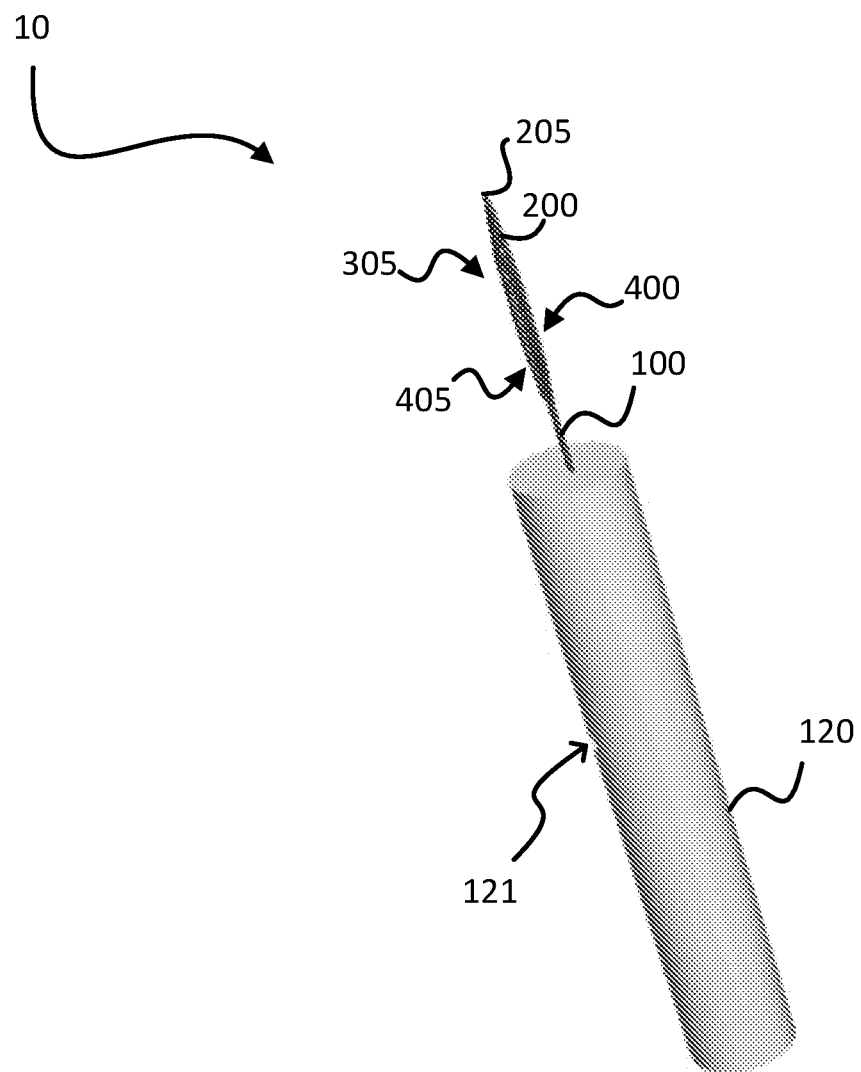
FIG. 3 is a side perspective view of the tissue cutting device of FIG. 1, showing the first blade and the second blade lying in the same plane when the second blade is in the first position.

The following detailed description is to be read with reference to the drawings, in which like elements in different drawings have like reference numerals. The drawings, which are not necessarily to scale, depict selected embodiments and are not intended to limit the scope of the invention. Skilled artisans will recognize that the examples provided herein have many useful alternatives that fall within the scope of the invention.

Referring to the drawings, and in particular, FIGS. 1-10, there is shown a tissue cutting device of the present disclosure generally represented by reference numeral 10. The tissue cutting device 10 can be used to cut any desired soft tissue structure in the body (e.g., of a human or non-human mammal). Such soft tissue structure includes, but is not limited to, a ligament, fascia, or tendon. In certain preferred embodiments, the tissue cutting device 10 is used to cut an A1 pulley.

In some embodiments, the tissue cutting device 10 includes a handle 100, a first blade 200, and a second blade 300 that collectively define a blade assembly. The first blade 200 is coupled to the second blade 300 and both blades 200, 300 are coupled to the handle 100. The first blade 200 is an exposed blade. As used in the present disclosure, an exposed blade refers to a blade that is not protected from contact with tissue. In contrast, an unexposed blade, as used in the present disclosure, refers to a blade that is protected from coming into contact with tissue by another structure of the device 10. The handle 100, the first blade 200, and the second blade 300 can have any desired size suitable for performing a particular cutting procedure. In addition, the handle 100 can be formed of any desired medically acceptable material.

As shown in FIGS. 1-5 and 10, the tissue cutting device 10 can optionally include a housing 120. In embodiments of this nature, the handle 100 is coupled to the housing 120 and extends outwardly (e.g., from a top end) of the housing 120. The handle 100 can be either permanently or removably coupled to the housing 120. Any conventional fastener can be used to couple the handle 100 to the housing 120, including but not limited to, screws, glue, or the like. FIGS. 1-5 and 10 show a non-limiting example of an embodiment where the handle 100 is screwed to the housing 120 via screws inserted into screw holes 121, 123.

In certain cases, the handle 100 is positionable within the housing 120. In other embodiments, the handle 100 is coupled to an exterior surface (e.g., top surface) of the housing 120 and does not extend into any portion of the housing 120. However, a housing 120 is not required in all cases, and it is envisioned that the housing 120 can be omitted in certain embodiments. In any embodiment of the present disclosure that includes the housing 120, it is preferred that the housing 120 has an ergonomic design configured to facilitate holding of the device 10.

Where the housing 120 is provided, the housing 120 can comprise a single-piece structure. In other instances, the housing 120 comprises multiple sections (FIG. 10), such as a first section 122 and a second section 124 that are coupled together. The sections 122, 124 of the housing 120 can be fixedly or removably coupled together. These sections 122, 124 can be coupled together in any conventional manner, such as by screws, snaps, glue or other adhesive. Other types of fasteners not explicitly recited herein can be used to couple together sections of the housing 120, and such alternative fasteners will be readily apparent to skilled artisans.

In some embodiments, an interior surface 126 of the housing 120 has a recess 130 formed therein. As can be appreciated by referring to FIG. 10, the recess 130 is sized and shaped such that the recess 130 is configured to receive the handle 100 when the handle 100 is coupled to the housing 120. Where the housing 120 includes the first section 122 and the second section 124, the recess 130 is formed in at least one of the first section 122 and the second section 124 (and optionally, both sections) of the housing 120. In certain other embodiments, the housing 120 does not include a recess 130.

In preferred embodiments, the second blade 300 and the handle 100 are integral structures. In some cases, the handle 100, the first blade 200, and the second blade 300 are all integral structures. In still further embodiments, the entire tissue cutting device 10 can be a single integral structure so as to define a unibody construction. In such instances, for example, the entire device 10 can comprise a single piece of metal (e.g., surgical grade stainless steel), plastic, or any other suitable material. In addition, the tissue cutting device 10 can be manufactured by any conventional process. As non-limiting examples, the tissue cutting device 10 can be stamped or laser cut.

Figure 4:
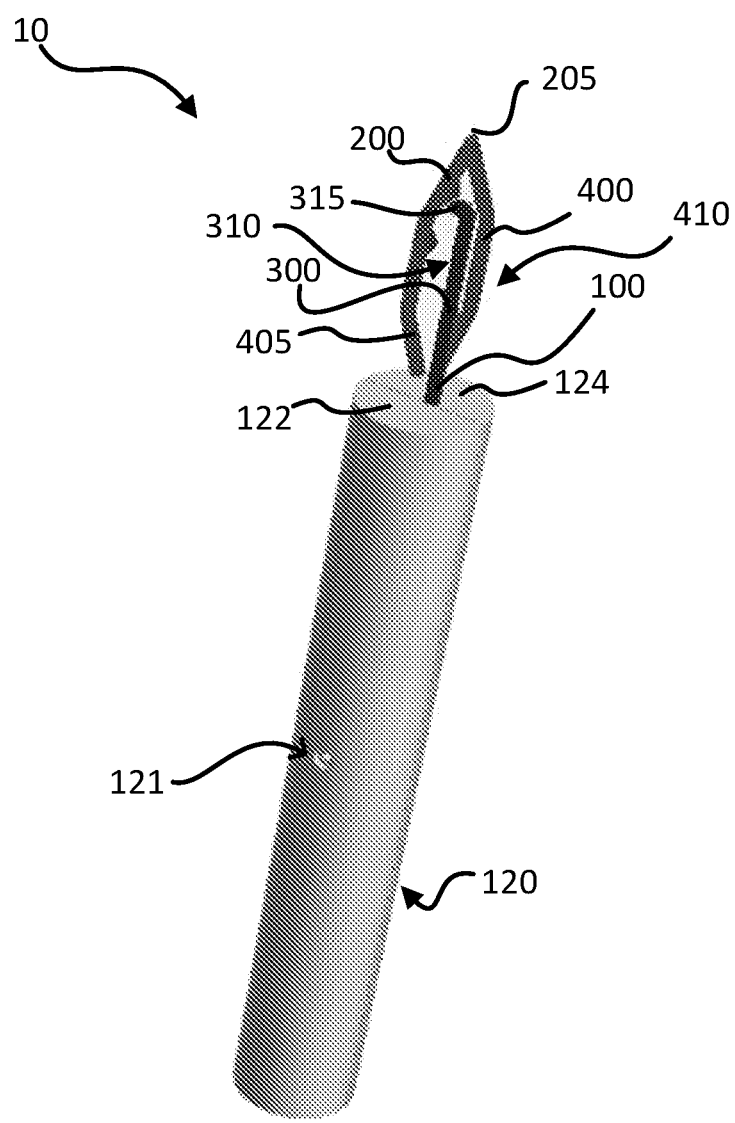
FIG. 4 is a top perspective of a tissue cutting device in accordance with certain embodiments of the present disclosure, showing a handle coupled to a housing and a second blade in a second (active) position.
Figure 5:
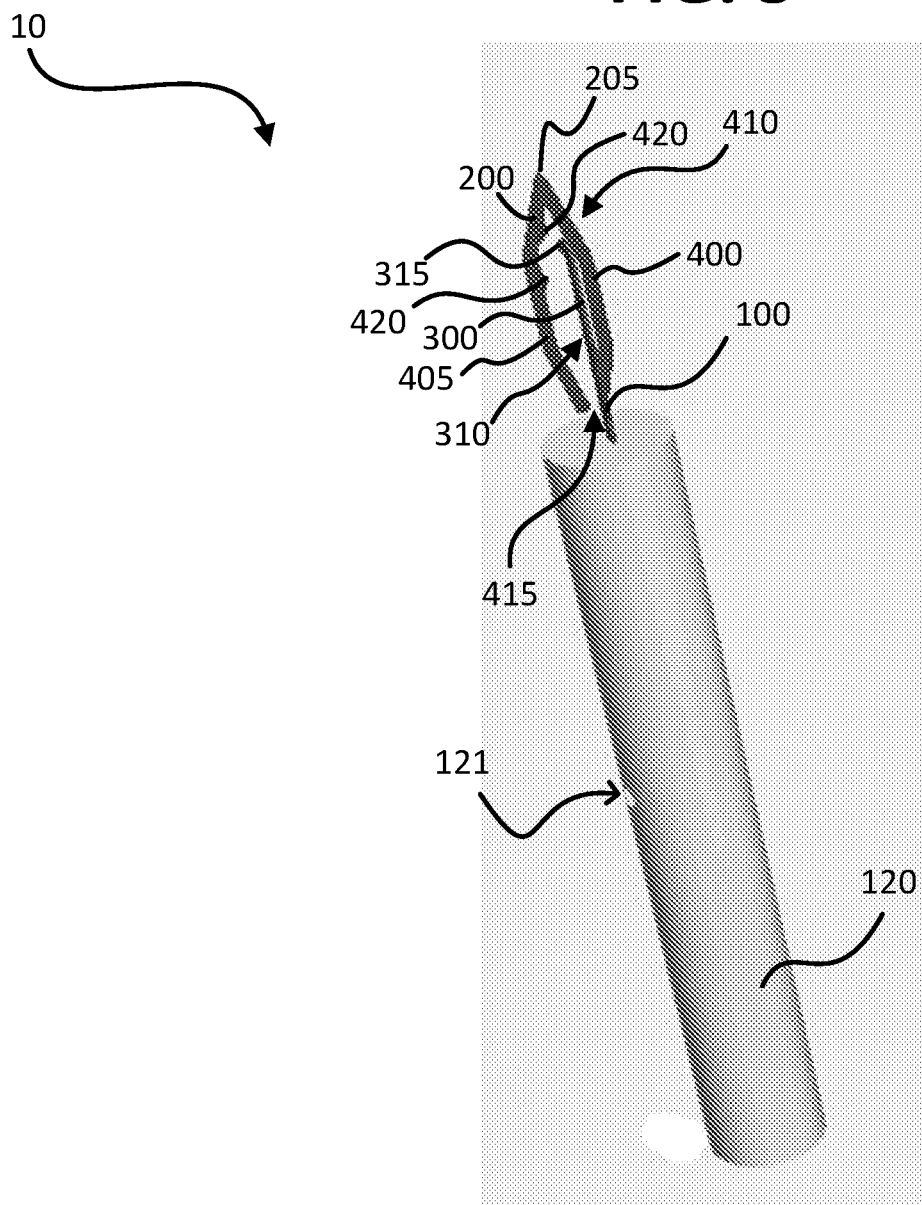
FIG. 5 is another top perspective view of the tissue cutting device of FIG. 4, showing the second blade in the second position.
Figure 6:
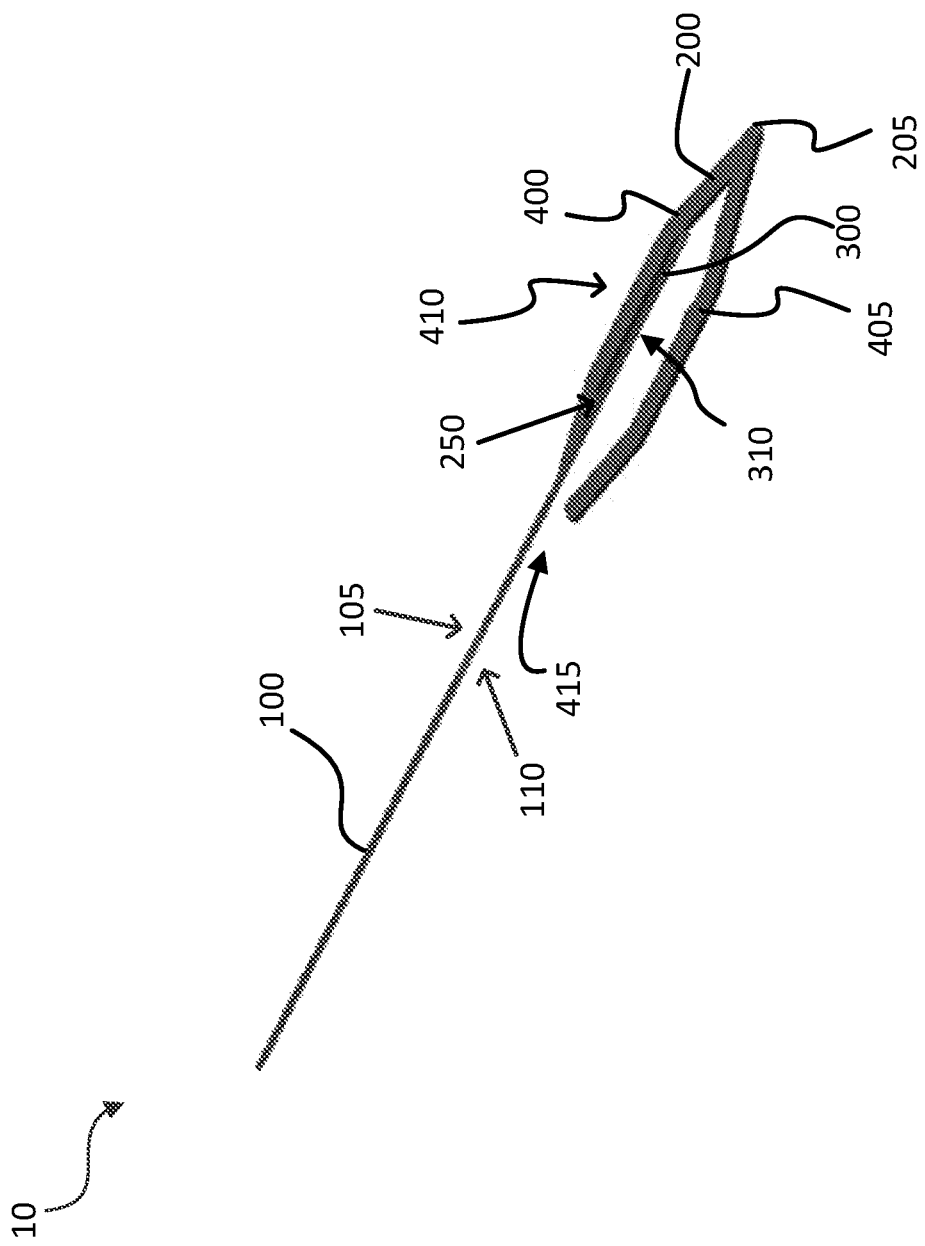
FIG. 6 is a side view of a tissue cutting device in accordance with certain embodiments of the present disclosure, showing a second blade in a second (active) position.
Figure 7:
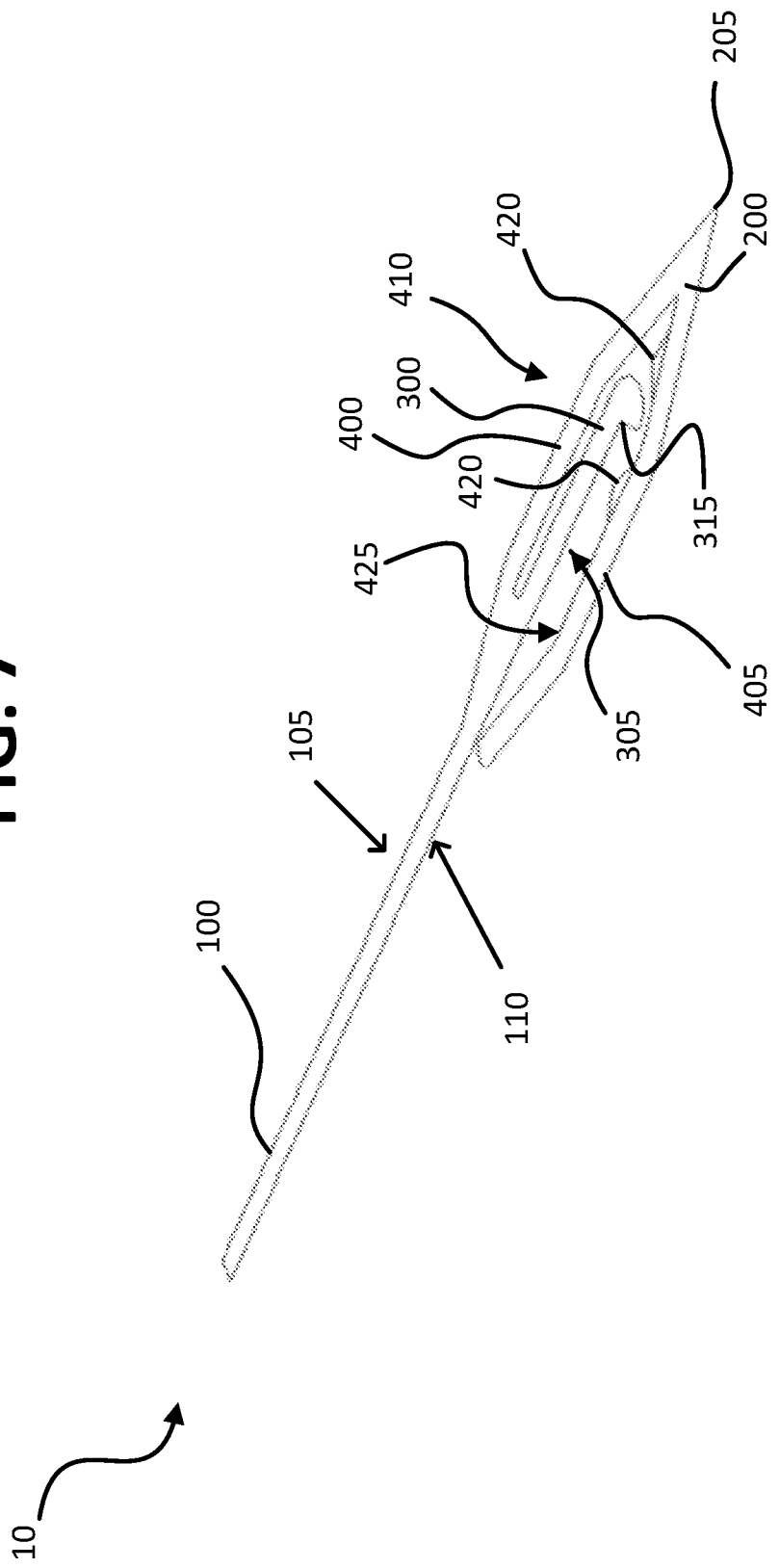
FIG. 7 is a schematic top perspective view of a tissue cutting device in accordance with certain embodiments of the present disclosure.
Figure 8:
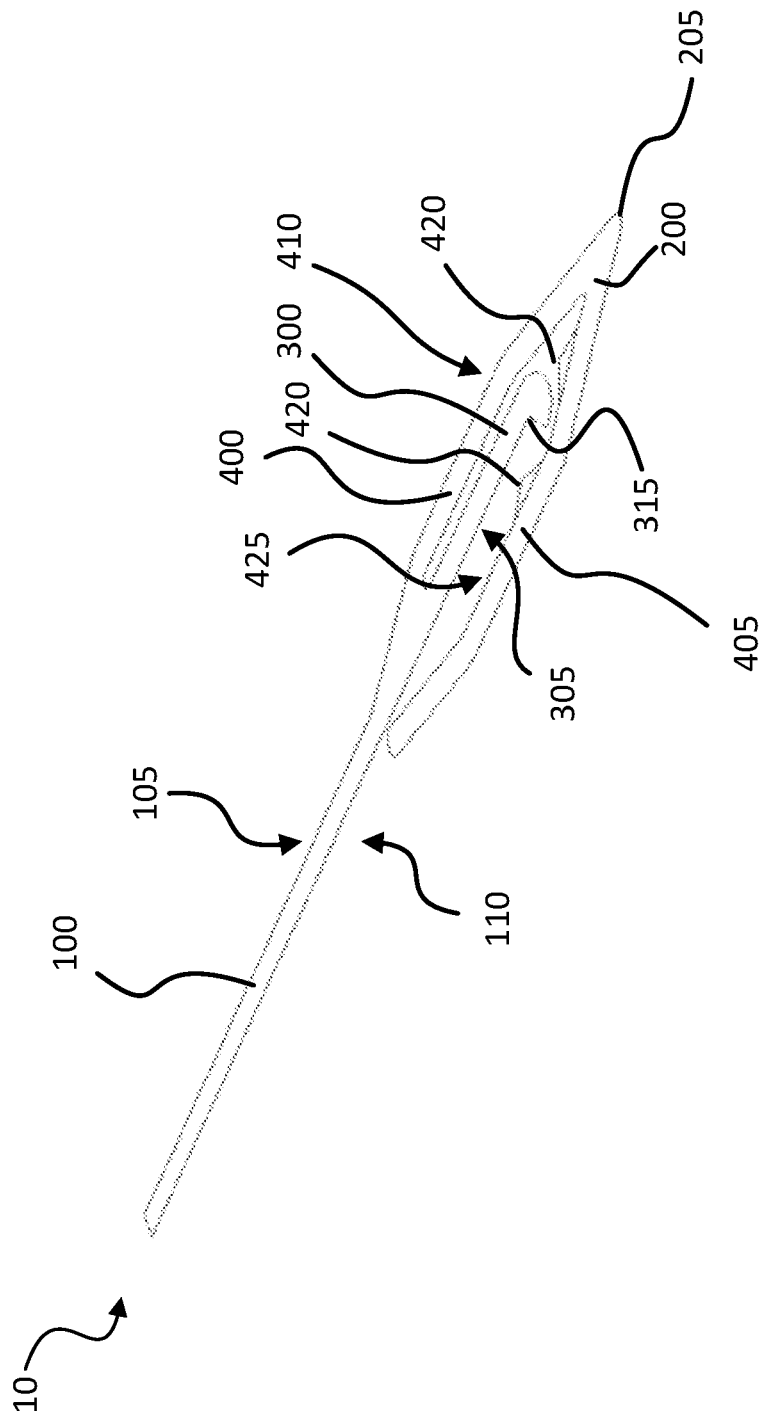
FIG. 8 is a schematic top perspective view of a tissue cutting device in accordance with certain embodiments of the present disclosure.
Figure 9:
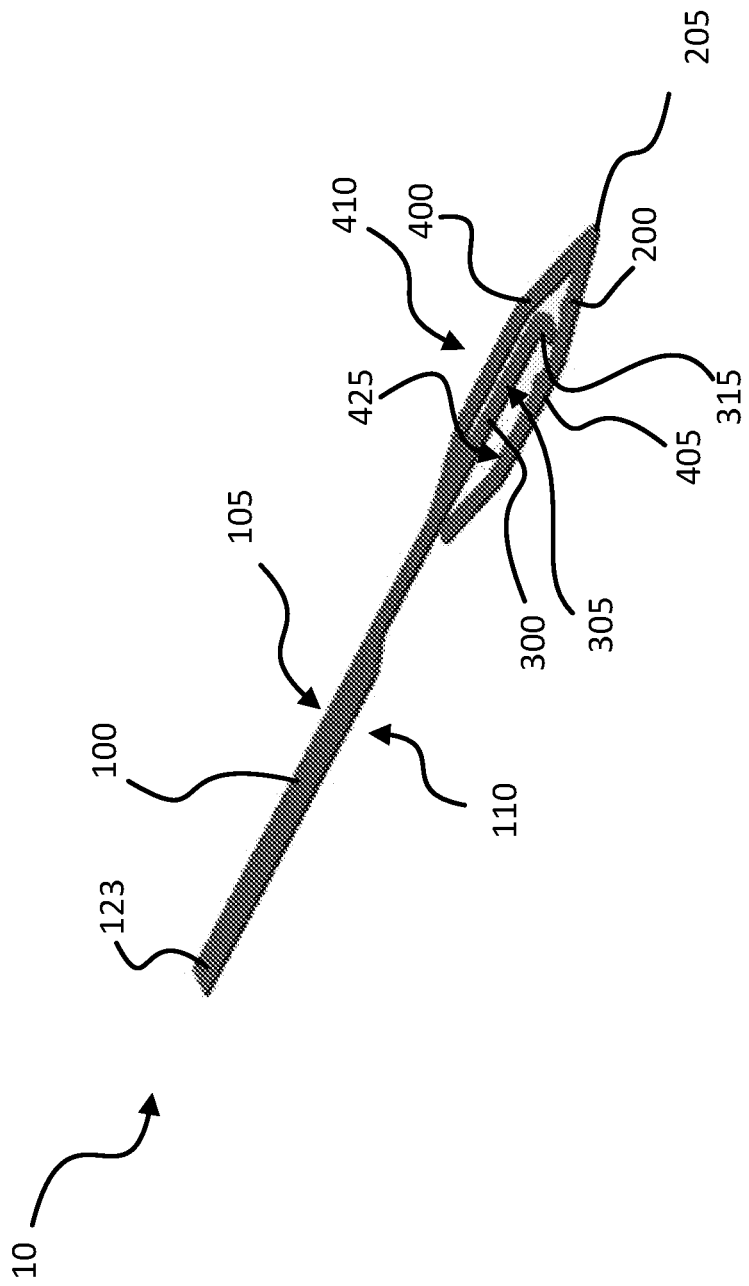
FIG. 9 is a top perspective view of a tissue cutting device in accordance with certain embodiments of the present disclosure.
Figure 10:
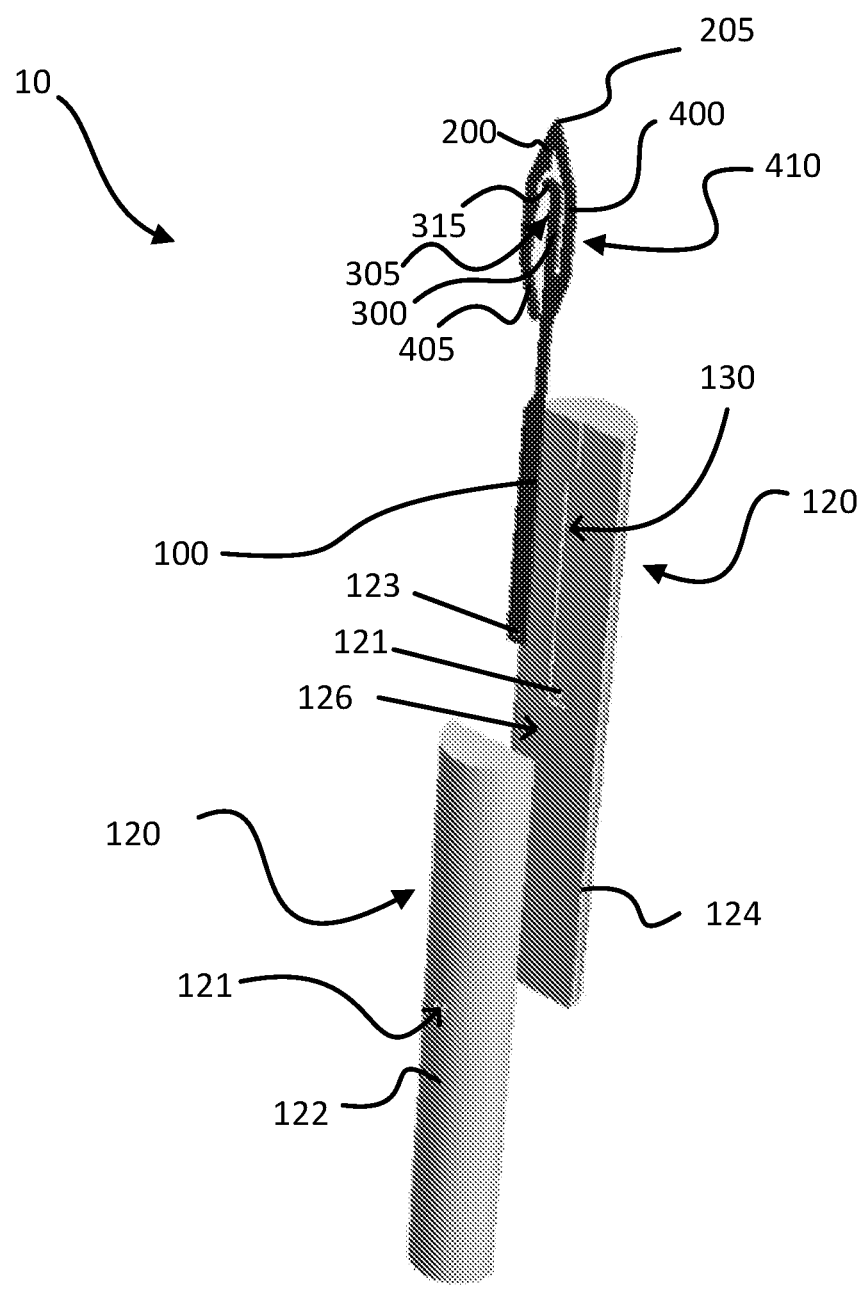
FIG. 10 is an exploded view of a tissue cutting device showing a blade assembly separated from a handle.

Advantageously, the second blade 300 is rotatable relative to the first blade 200 such that the second blade 300 is configured to rotate between a first (inactive) position 305 (FIGS. 1-3 and 7-10) and a second (active) position 310 (FIGS. 4-6). The second blade 300 is in a same plane as the first blade 200 when the second blade 300 is in the first position 305. This is perhaps best illustrated in FIG. 3, which shows that the first blade 200 and the second blade 300 lie flat (i.e., parallel or substantially parallel) relative to each other when the second blade 300 is in the first position 305. This arrangement of the tissue cutting device 10 provides a low-profile design that enables the tissue cutting device 10 to be inserted into tight spaces underneath a patient's skin, adjacent a desired tissue region.

The second blade 300 is rotated into a different plane from the first blade 200 as the second blade 300 is rotated from the first position 305 toward the second position 310. As described in greater detail below, when the second blade 300 is in the first (inactive) position 305, the second blade 300 is an unexposed blade that is protected (at least in part) by the first blade 200. The second blade 300 can remain in the first position 305 until needed for a cutting procedure. Then, when it is desired to cut tissue using the second blade 300, the second blade 300 is rotated into the second (active) position 310, thereby becoming an exposed blade.

In certain embodiments, the tissue cutting device 10 is hingeless. In such embodiments, as shown in FIGS. 1-10, the material properties and design (including the shape of device 10, as well as the thickness and flexibility of the second blade 300) allow the second blade 300 to intrinsically bend relative to the first blade 200. The second blade 300 should be thin enough to allow the second blade 300 to bend to permit its rotation between the first 305 and second 310 positions. The second blade 300 is capable of being bent in a manner that is similar to bending of a paper clip (i.e., whereby twisting an inner portion of a metal paper clip allows the inner portion to be rotated and positioned outside of an outer portion of the paper clip).

In other embodiments, the tissue cutting device 10 includes one or more hinges. Any type of conventional mechanical hinge(s) can be used in tissue cutting device 10 to allow second blade 300 to rotate between its first 305 and second 310 positions. In other cases, the second blade 300 is provided with one or more virtual hinges, such as one or more seams that extend (e.g., longitudinally in series) along a longitudinal axis of the second blade 300. In such instances, the one or more seams extend along the second blade 300 at one or more locations where the second blade 300 is materially coupled to the first blade 200 such that the one or more seams are provided at junction(s) 250 of the first blade 200 and the second blade 300. The second blade 300 can be thinner in the region where the one or more seams are located so as to reduce resistance of the second blade 300 to bending. In this manner, the one or more seams facilitate folding and bending of the second blade 300 along the second blade's longitudinal axis for rotating the second blade 300 from its first position 305 toward its second position 310. Thus, the one or more seams allow the second blade 300 to move from its first position 305 toward its second position 310 without separating the first blade 200 from the second blade 300.

The second blade 300 rotates between the first position 305 and the second position 310 in response to rotation of the handle 100. Thus, the second blade 300 and the handle 100 rotate together. The first blade 200 is configured to remain stationary or substantially stationary when the second blade 300 rotates from the first position 305 toward the second position 310. The second blade 300 is configured to rotate along its longitudinal axis when the second blade 300 rotates between the first position 305 and the second position 310. In preferred embodiments, the handle 100 is aligned (or substantially aligned) with the longitudinal axis of the second blade 300 such that the second blade 300 defines a linear extension of the handle 100.

The second blade 300 can have any desired degree of rotation as needed to suit a particular cutting procedure. In some instances, the second blade 300 is configured to rotate in a range of between 0 to 180 degrees, including any degree therebetween. In other cases, the second blade 300 is configured to rotate in a range of between 0 and 90 degrees (including any degree therebetween).

The first blade 200 is configured to facilitate introduction of the tissue cutting device 10 through the dermis and into subcutaneous tissue of a patient. In this manner, the first blade 200 eliminates the need for the use of a separate, additional device to introduce the tissue cutting device 10 into the skin. Instead, in some embodiments, the tissue cutting device 10 has both the first blade 200 to introduce the device 10 into the skin, and the second blade 300 that can be unexposed and protected until needed to cut or release the tissue of interest.

The first blade 200 has a distal end 205. In some cases, the outer surface of the first blade 200 includes one or more cutting surfaces. In other cases, the distal end 205 of the first blade 200 defines a tip not intended for cutting tissue. For example, in certain cases, the distal end 205 defines a blunt tip (e.g., a rounded, convex end) not intended for cutting tissue. In other cases, the distal end 205 defines a sharp-edged tip intended for cutting tissue. For example, in some cases, the distal end 205 defines a dissecting tip or a cutting tip. The configuration of the distal end 205 of the first blade 200 is not particularly limited. For instance, the distal end 205 of the first blade 200 can include a pointed tip (FIG. 7), a curved edge (FIG. 8 and FIG. 21), a straight edge of uniform length, an angled surface that is longer on one side than on the other, or can have any other desired configuration. In addition, the one or more cutting surfaces of the first blade 200 (where provided) can extend along the entire outer surface of the first blade 200, along a major length of the outer surface of the first blade 200 (i.e., along a length that is greater than 50% of a length of the outer surface), or along only a minor portion of the outer surface of the first blade 200, such as only at the distal end 205.

The second blade 300 also has at least one cutting surface 315. In some embodiments, the cutting surface 315 of the second blade 300 is less sharp than the cutting surface and/or distal end 205 of the first blade 200. In other cases, the cutting surface 315 of the second blade 300 is sharper than some (or all) of the outer surface of the first blade 200. In still yet other cases, the cutting surface 315 of the second blade 300 has the same sharpness as the outer surface (or as the cutting surface) of the first blade 200.

The configuration of the cutting surface 315 of the second blade 300 is also not limited. The cutting surface 315 can be a single cutting surface or one of many cutting surfaces. Also, the cutting surface 315 can be a curved surface, a straight surface (of uniform length), or an angled surface that is longer on one side than on the other side (e.g., a downward-angled cutting surface). In addition, the cutting surface 315 can face toward or away from the handle 100, or can face toward either side of the tissue cutting device 10. In some cases, the cutting surface 315 is provided on an interior surface of the second blade 300. In other cases, the cutting surface 315 is provided on an outer surface of the second blade 300 (e.g., so as to provide a superficial cutting surface). In certain embodiments, the cutting surface 315 of the second blade 300 is a retrograde cutting surface configured to facilitate cutting of tissue when the second blade 300 is moved in a retrograde manner. In other cases, the cutting surface 315 of the second blade 300 is an antegrade cutting surface configured to facilitate cutting of tissue when the second blade 300 is moved in an antegrade manner. In yet other cases, the cutting surface 315 is both a retrograde and antegrade cutting surface. Skilled artisans will understand that the examples identified herein are not limiting, and that any type of cutting surface can be used as cutting surface 315. Various cutting surfaces 315 are shown in the figures. Skilled artisans will appreciate that the cutting surfaces 315 shown in FIGS. 22B, 23B, 24B, 25B, 26B, and 27B can be provided in any embodiment of the present disclosure.

Although only one cutting surface 315 is shown in the drawings, the second blade 300 can have any desired number of cutting surfaces 315, each having any desired configuration. In some cases, the second blade 300 is provided with a single cutting surface 315. In other cases, the second blade 300 has more than one cutting surface 315 to allow the tissue cutting device 10 to achieve cuts in multiple directions.

In any embodiment of the present disclosure, the second blade 300 is optionally echogenic. In embodiments of this nature, the second blade 300 can have a flat superficial surface, etching, or an echogenic coating, with each of these features being designed to improve visualization of the second blade 300 under ultrasound.

The tissue cutting device 10 further includes a first arm 400 and a second arm 405. The first arm 400 and the second arm 405 define opposite sides of the first blade 200. The first arm 400 is coupled to and extends between the first blade 200 and a first side 105 of the handle 100. In preferred embodiments, the first arm 400 is coupled directly to the handle 100. The second arm 405 is coupled to the first blade 200 and extends from the first blade 200 toward a second side 110 of the handle 100. However, unlike the first arm 400, the second arm 405 does not contact any portion of the handle 100 (or the second blade 300). This space between the second arm 405 relative to both the handle 100 and the second blade 300 defines a gap 415. As described in greater detail below, the second arm 405 is configured to stabilize the tissue cutting device 10 (particularly the first blade 200 and the first arm 400) when the second blade 300 is rotated from the first position 305 to the second position 310. In particular, the gap 415 allows only a portion of the tissue cutting device to rotate (i.e., the handle 100 and the second blade 300), while a remainder of the device 10 is configured to remain stationary or substantially stationary.

When the second blade 300 is in the first position 305, the cutting surface 315 of the second blade 300 is positioned between (e.g., directly between) the handle 100 and the first blade 200. In more detail, the second blade 300 is located between the handle 100, the first blade 200, the first arm 400, and the second arm 405 when the second blade 300 is in the first position 305. Thus, the handle 100, the first blade 200, the first arm 400, and the second arm 405 define an outer enclosure 410 surrounding the second blade 300 when the second blade 300 is in the first position 305. This outer enclosure 410 protects the second blade 300 from contacting tissue when the second blade 300 is in the first position 305.

The second blade 300 is configured to rotate outside of the outer enclosure 410 when the second blade 300 is rotated from the first position 305 toward the second position 310. Rotation to the second position 310 allows the second blade 300 to be exposed for cutting tissue, since the second blade 300 is no longer protected by the outer enclosure 410. In some cases, as shown in FIGS. 1-10, the outer enclosure 410 has a convex or substantially convex shape. However, alternative configurations for the outer enclosure 410 are also contemplated and within the scope of the present disclosure.

As the second blade 300 rotates from the first position 305 toward the second position 310, the second arm 405 does not rotate (or at least remains stationary or substantially stationary). This is at least in part due to a greater surface area of the second arm 405 as compared to a surface area of the second blade 300. In particular, the second blade 300 is thin enough to rotate when introduced subcutaneously into the skin near a tissue region of interest. The second arm 405, on the other hand, is held down by the tissue or other structure to be cut and therefore is restrained from rotating when the second blade 300 rotates from the first position 305 toward the second position 310.

In some cases, at least one tooth 420 is coupled to an interior surface 425 of at least one of the first arm 400 and the second arm 405. In some cases, the at least one tooth 420 includes two or more teeth or a plurality of teeth. The at least one tooth 420 can be coupled to the only the first arm 400, only the second arm 405, or to both the first arm 400 and the second arm 405. The at least one tooth 420 is perhaps best shown in FIGS. 7 and 8, where it is depicted as two teeth. The at least one tooth 420 is configured to embed into the undersurface of the structure to be cut (e.g., the A1 pulley) to ensure that the device 10 will not slide during use. The cutting surface 315 of the second blade 300 can extend outwardly toward the second arm 405 such that the at least one tooth 420 is positioned on an arm that is nearest the cutting surface 315.

Figure 21:
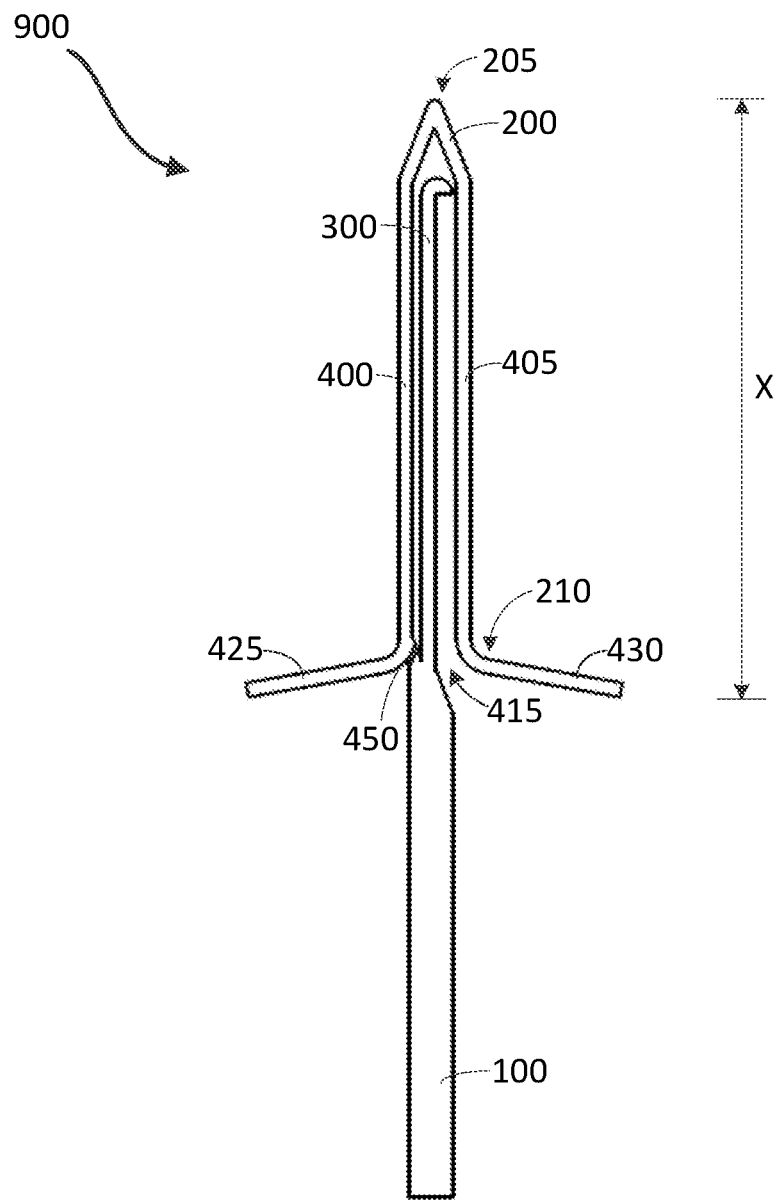
FIG. 21 is a schematic top perspective view of a tissue cutting device having one or more break points in accordance with certain embodiments of the present disclosure.
Figure 22B:
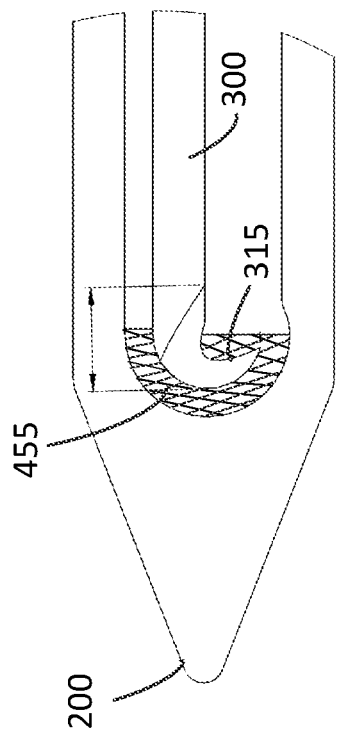
FIG. 22B is a detailed view of the first and second blades shown in FIG. 22A.
Figure 22A:
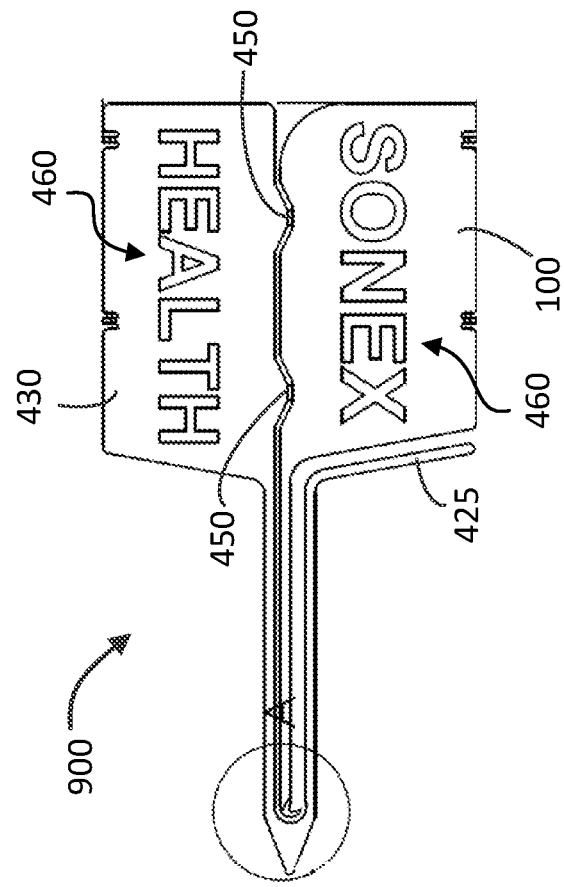
FIG. 22A is a schematic view of a tissue cutting device having one or more break points in accordance with certain embodiments of the present disclosure.
Figure 25A:
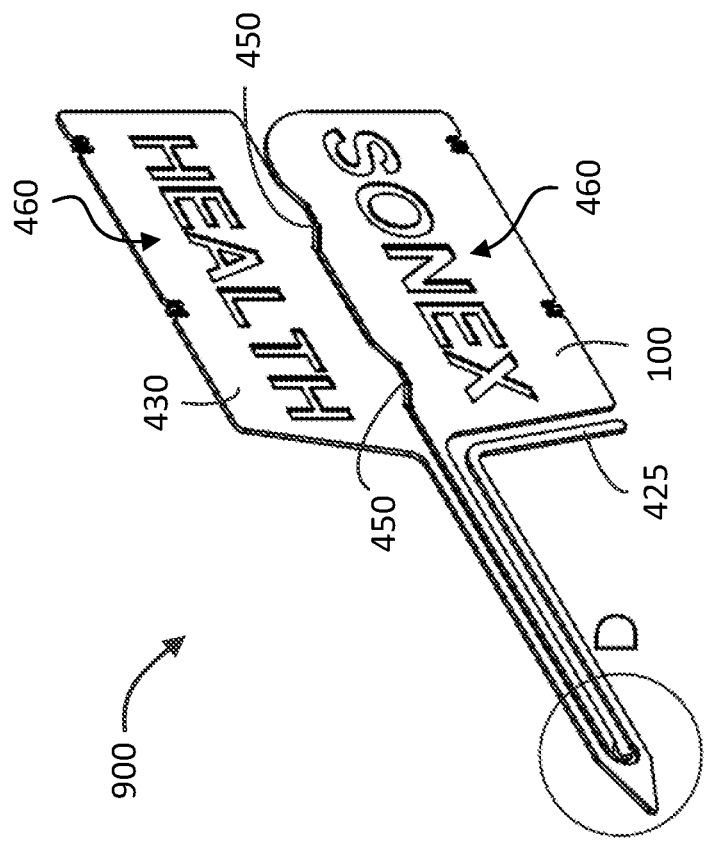
FIG. 25A is a schematic view of a tissue cutting device having one or more break points in accordance with certain embodiments of the present disclosure.
Figure 25B:
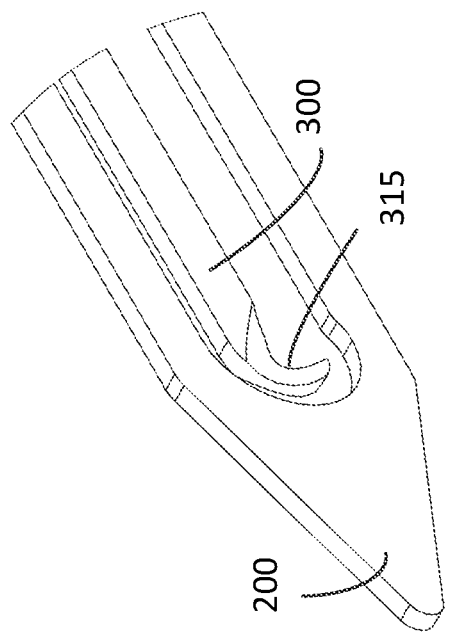
FIG. 25B is a detailed view of the first and second blades shown in FIG. 25A.
Figure 26A:
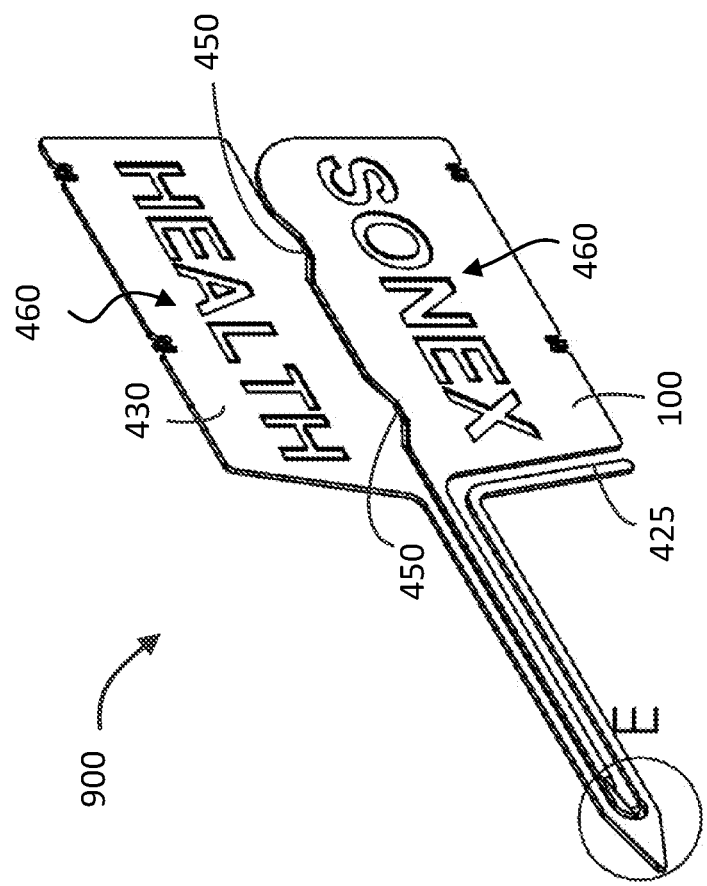
FIG. 26A is a schematic view of a tissue cutting device having one or more break points in accordance with certain embodiments of the present disclosure.
Figure 26B:
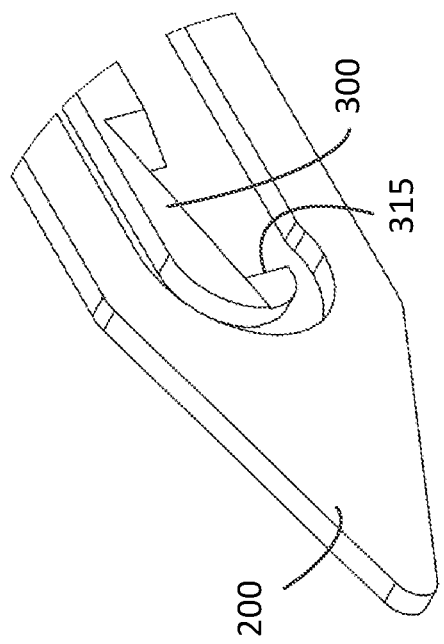
FIG. 26B is a detailed view of the first and second blades shown in FIG. 26A.
Figure 27B:
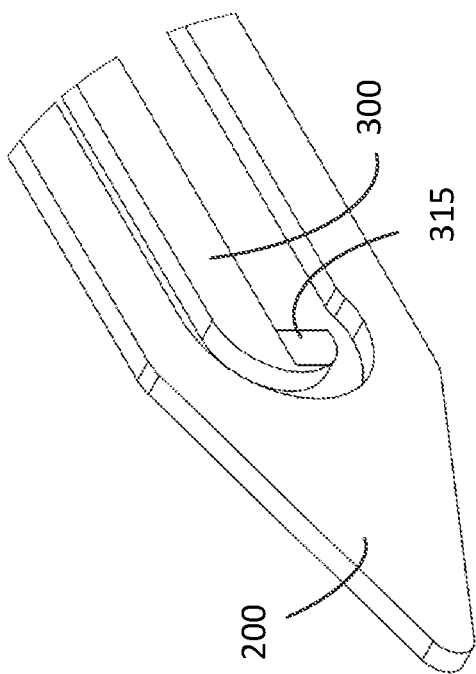
FIG. 27B is a detailed view of the first and second blades shown in FIG. 27A.
Figure 27A:
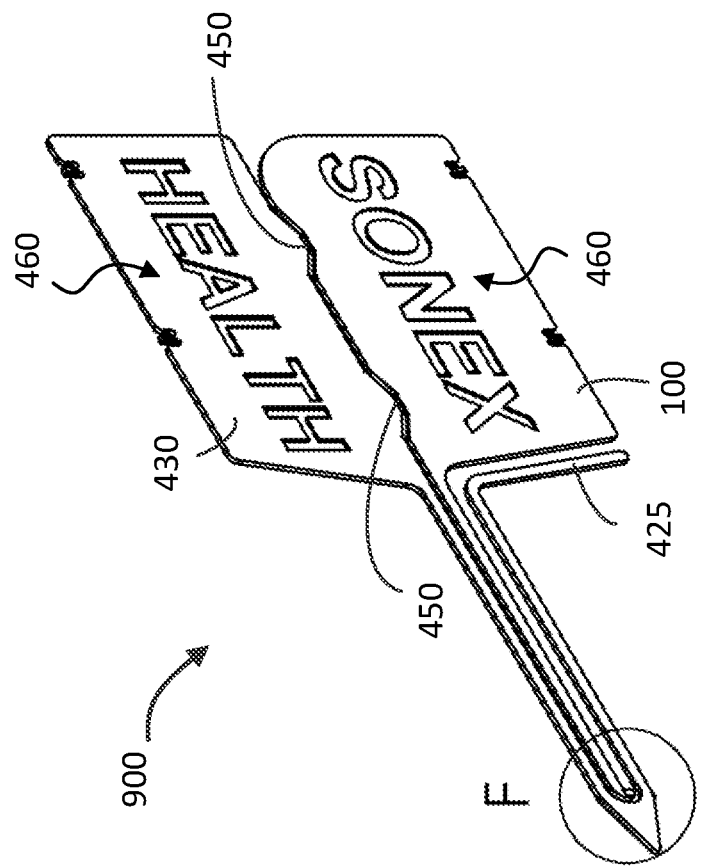
FIG. 27A is a schematic view of a tissue cutting device having one or more break points in accordance with certain embodiments of the present disclosure.

Another exemplary embodiment of a tissue cutting device 900 is shown in FIG. 21. Tissue cutting device 900 can optionally include any of the features previously described for FIGS. 1-10. This embodiment includes a first blade 200 and a second blade 300 and further includes one or more break points 450 between the first blade 200 and the second blade 300. The one or more break points 450 are configured to be disrupted. The one or more break points 450 allow an operator to disrupt the one or more break points 450 and separate the first blade 200 from the second blade 300. When the one or more break points 450 are intact, the second blade 300 is its first position 305. When force is applied to each of the one or more break points 450 to separate the first blade 200 from the second blade 300, the second blade 300 assumes its second position 310.

Generally, the first blade 200 is coupled to the handle 100 via the one or more break points 450, which are configured to break the first blade 200 away from the handle 100. The second blade 300 is also coupled to the handle 100 but does not include any break points. In other words, the second blade 300 is configured to remain connected to the handle 100 and does not break away from the handle 100. In some cases, the second blade 300 is integral to the handle 100. The one or more break points 450 allow an operator to break away or separate the first blade 200 from the handle 100, thus separating the first blade 200 from the second blade 300 and the handle 100. In certain cases, the one or more break points 450 are configured to be disrupted when the second blade 300 is rotated from the first position 305 toward the second position 310.

Referring to FIG. 21, certain embodiments include a first blade 200 that includes a distal end 205 and a proximal end 210. The first blade 200 extends for a length "X" along its longitudinal axis from the distal end 205 to the proximal end 210. The first blade 200 also includes a first arm 400 and a second arm 405. The first arm 400 and the second arm 405 define opposite sides of the first blade 200. Each the first arm 400 and the second arm 405 extend along the longitudinal axis between the distal end 205 and a proximal end 210.

The first arm 400 is coupled to the handle 100 at the one or more break points 450. The second arm 405 is not coupled to the handle 100. Rather, the second arm 405 does not contact any portion of the handle 100. A gap 415 is provided between the second arm 405 and the handle 100. The one or more break points 450 can be provided anywhere along the first arm 400. In certain cases, the one or more break points 450 are positioned on the first arm 400 such that the one or more break points 450 are adjacent to the proximal end 210.

The one or more break points 450 are configured to break the first arm 400 from the handle 100 upon force. In other words, an operator applies force to the one or more break points 450 to disrupt them and therefore separate the first arm 400 (and thus the first blade 200) from the handle 100 (and thus the second blade 300). The one or more break points 450 can include any mechanism that allows force to break away the first arm 400 from the handle 100. In certain cases, each of the one or more break points 450 is formed as a break-away seam. In other cases, each of the one or more break points 450 is formed as a break-away hinge. Such break-away seams or hinges can include snap perforations or frangible bridges that allow force to break away the first arm 400 from the handle 100.

In certain embodiments, an operator uses rotational force to break away the first arm 400 from the handle 100. For example, an operator rotates the handle 100 in either a clockwise or counterclockwise direction to disrupt the one or more break points 450. In other embodiments, an operator uses shear force (e.g., a pushing or pulling force). Any number of break away mechanisms are contemplated.

Some embodiments also provide one or more flanges that extend outward from the first blade 200. The one or more flanges are sized and shaped to accommodate an operator's fingers. An operator can grasp the one or more flanges to assist in manipulating the first blade 200. In certain cases, the one or more flanges extend radially outward from the longitudinal axis of the first blade 200. In some cases, the one or more flanges extend generally perpendicular from the longitudinal axis of the first blade 200. In some cases, the one or more flanges are provided as a first flange and a second flange. The first flange and second flange can extend outward as a pair of wings, similar to flanges of a medical syringe. In other cases, the one or more flanges are provided as a single circular flange that surrounds the first blade 200. A variety of different types of flanges are contemplated.

In the embodiment of FIG. 21, the first blade 200 includes a first flange 425 and a second flange 430. The first flange 425 extends from the first arm 400 and the second flange 430 extends from the second arm 405. Also, the first flange 425 extends radially outward from the first arm 400 and from the longitudinal axis of the first blade 200, and the second flange 430 extends radially outward from the second arm 405 and from the longitudinal axis of the first blade 200. In some cases, the first flange 425 and the second flange 430 can each extend generally perpendicular to the longitudinal axis, although this is not required.

As shown in FIG. 21, both the first flange 425 and the second flange 430 are positioned near a proximal end 210 of the first blade 200. The first blade 200 is also provided with a length "X," which is the length between the distal end 205 and the proximal end 210. The length "X" is selected to be a maximum length of where the first blade 200 should be inserted into the body. The first flange 425 and the second flange 430 therefore prevent the first blade 200 from being inserted beyond the selected maximum length and therefore prevent it from being inserted too deeply into the body. The flanges 425, 430 also allow manipulation and stabilization of the whole device (including the handle 100, first blade 200 and second blade 300) before separation of the first blade 200 from the handle 100.

Once the first blade 200 is separated from the handle 100, an operator can move the second blade 300 independently of the first blade 200. In some cases, an operator can rotate the second blade 300 in a range of between 0 to 360 degrees. Any desired movement is possible since the second blade 300 is independent of the first blade 200. An operator then uses the handle 100 to manipulate the second blade 300 to perform the desired cutting. Once cutting is completed, the operator pulls the handle 100 and thus the second blade 300 out of the body. The flanges 425, 430 also allow manipulation and stabilization of the first blade 200 after separation from the second blade 300. For example, an operator can grasp the flanges 425, 430 with fingers and pull the first blade 200 out of the body.

One or more grip-enhancing features 460 can optionally be provided for any tissue cutting device of the present disclosure. The grip-enhancing feature(s) 460 are configured to improve the operator's ability to grip the tissue cutting device. In some cases, the one or more grip-enhancing features 460 are provided on the handle 100 and/or the flange(s) 425, 430. In some cases, the one or more grip-enhancing features 460 comprise etching, texture, and/or marking indicia (e.g., logos, text, etc.). These examples, however, are by no means limiting, and skilled artisans will appreciate that any grip-enhancing features can be used. In the embodiments shown in FIGS. 22A, 23A, 24A, 25A, 26A, and 27A, the one or more grip-enhancing features 460 comprise text (e.g., letters) on the handle 100.

In certain embodiments, the first blade 200 comprises a lip 455. When the second blade 200 is in the first position 305, the lip 455 is configured to surround the cutting surface 315 of the second blade 300 such that the cutting surface 315 of the second blade 300 rests upon the lip 455. In this manner, the lip 455 is configured to keep the cutting surface 315 of the second blade 300 from being deflected out of plane with respect to the first blade 200 while the second blade 300 is not intended to be used for cutting. Although the lip 455 is shown only in FIG. 22B, such a lip can be provided in any embodiment of the present disclosure.

Although certain embodiments describing one or more break points 450 have been described, in some cases, the one or more break points 450 are omitted and replaced with one or more hinges. In such cases, the one or more hinges are provided in location(s) where the one or more break points 450 would otherwise be located. In such instances, the one or more hinges enable the second blade 300 to rotate relative to the first blade 200, but does not allow the first blade 200 to be separated from the second blade 300. In other words, the first blade 200 is configured to remain connected to the handle 100 and does not break away from the handle 100 (such that the first blade 200 and the second blade 300 also remain connected). In embodiments of this nature, any type of conventional mechanical hinge(s) can be used to allow second blade 300 to rotate between its first 305 and second 310 positions. In other cases, one or more virtual hinges, such as one or more seams, are provided. In such instances, the one or more virtual hinges (e.g., the one or more seams) extend along the first blade 200 at one or more locations where the first blade 200 is materially coupled to the handle 100. In embodiments where one or more hinges are provided, the second blade 300 is able to rotate relative to the first blade 200 in a similar manner to the other hinge embodiments described herein (e.g. by rotating the handle 100).

The present disclosure also provides tissue cutting device 500, shown in FIGS. 11-20. As with tissue cutting device 10, tissue cutting device 500 can be used to cut any desired soft tissue structure in the body (e.g., of a human or non-human mammal). Such soft tissue structure includes but is not limited to, a ligament, fascia, or tendon. In certain embodiments, the tissue cutting device 500 is used to cut an A1 pulley.

Figure 13:
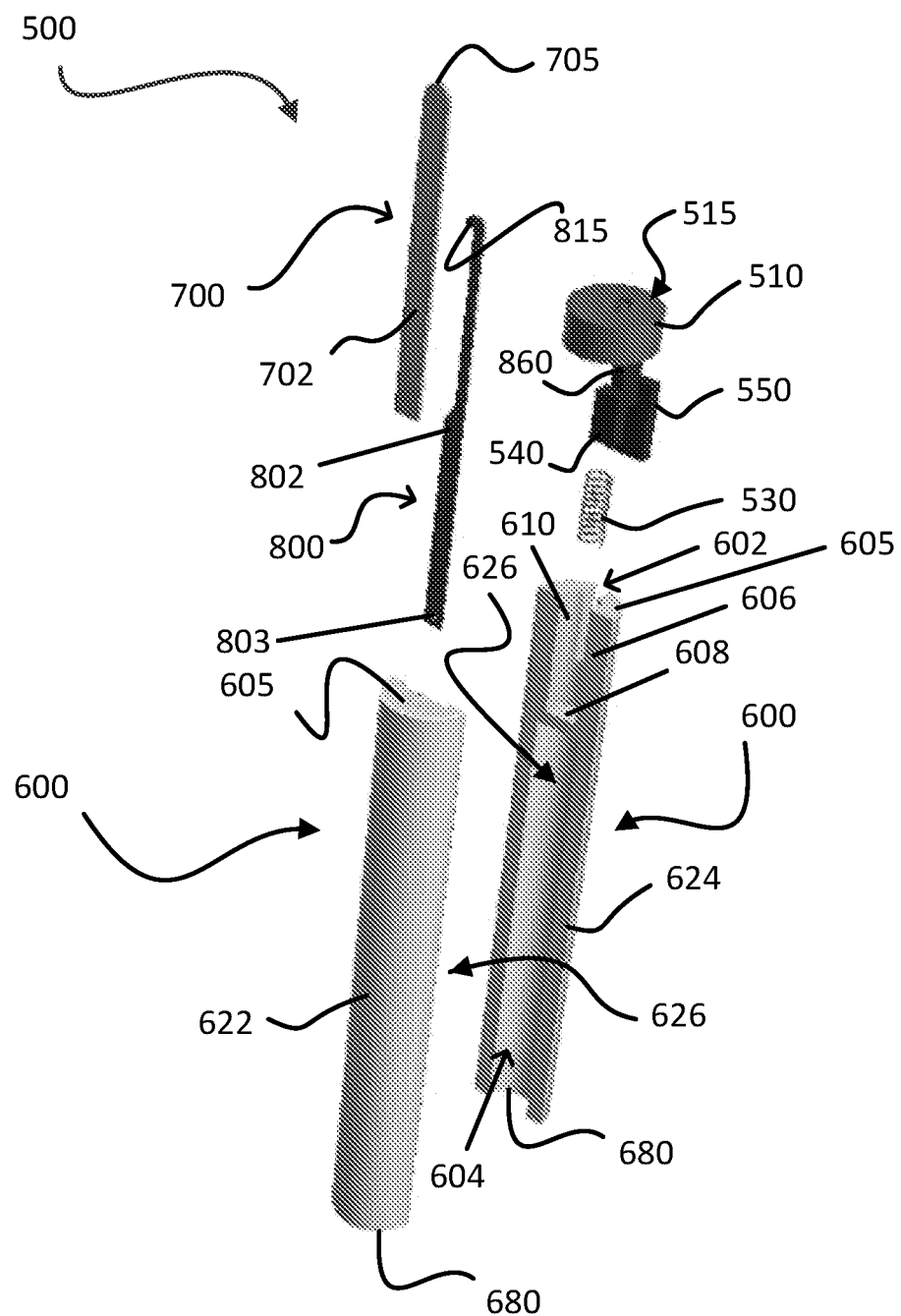
FIG. 13 is an exploded view of the tissue cutting device of FIG. 11.
Figure 14:
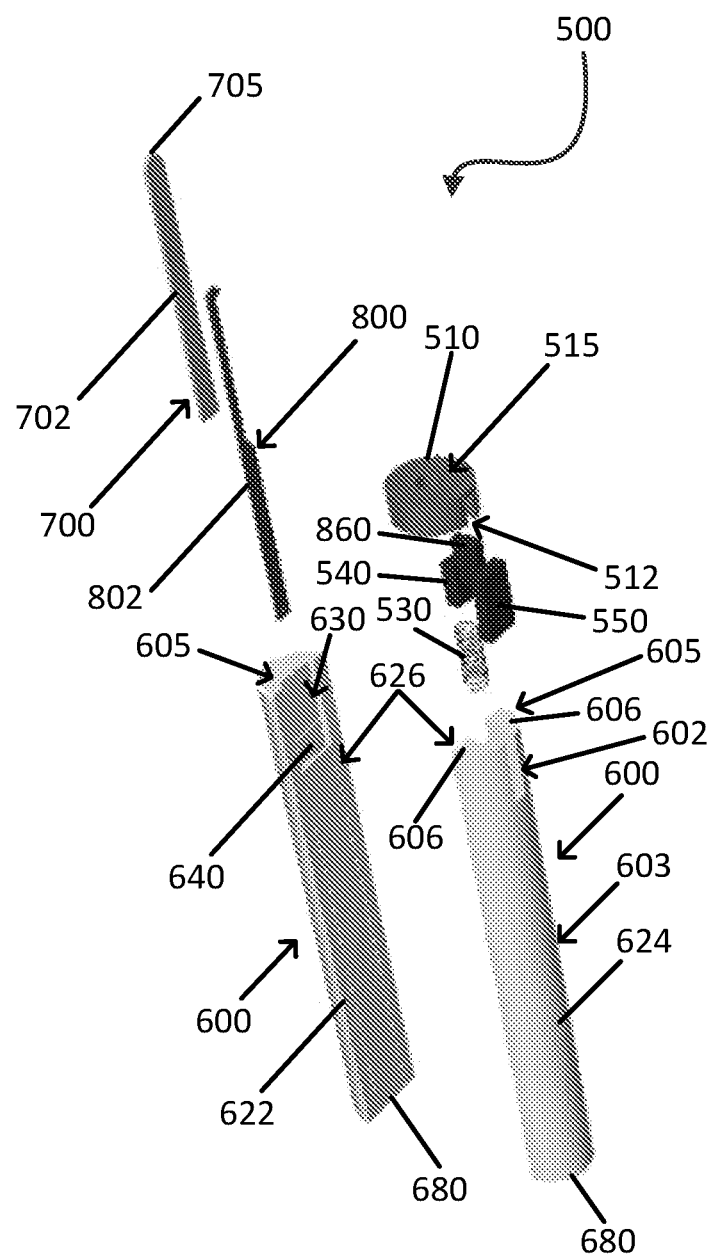
FIG. 14 is another exploded view of the tissue cutting device of FIG. 11.

Similar to cutting device 10, cutting device 500 has a handle 600, a first blade 700, and a second blade 800. The first blade 700 extends away from the handle 600. The second blade 800 is coupled to and extends outwardly from the handle 600. In some cases, the second blade 800 is screwed to the handle 600. For example, as shown in FIGS. 13 and 14, the handle 600 and the second blade 800 can have screw holes 640, 803 formed therein for connecting the second blade 800 to the handle 600. However, it will be appreciated that any conventional fastener, including but not limited to, screws, glue or other adhesive, can be used to couple the second blade 800 to the handle 600. Furthermore, the handle 600 preferably has an ergonomic design configured to facilitate holding of the device 500.

Similar to cutting device 10, the handle 600, the first blade 700, and the second blade 800 of cutting device 500 can have any desired size suitable for performing a particular cutting procedure. In addition, the handle 600 can be formed of any desired medically acceptable material.

The first blade 700 is similar to the first blade 200 of device 10. In particular, the first blade 700 is configured to facilitate introduction of the tissue cutting device 500 through the dermis and into subcutaneous tissue of a patient. In this manner, the first blade 700 eliminates the need for the use of a separate, additional device to introduce the tissue cutting device 500 into the skin. Instead, in some embodiments, the tissue cutting device 500 has both the first blade 700 to introduce the device 500 into the skin, and the second blade 800 that can be unexposed and protected until needed to cut or release the tissue of interest.

The first blade 700 has a shaft 702. The shaft 702 includes a distal end 705 provided on an outer surface of the first blade 700. In some cases, the distal end 705 of the first blade 700 includes one or more cutting surfaces. In other cases, the distal end 705 of the first blade 700 defines a blunt tip that is not intended for cutting tissue. The configuration of the distal end 705 of the first blade 700 is not particularly limited. For instance, the distal end 705 of the first blade 700 can include a pointed tip, a curved edge, a straight edge of uniform length, an angled surface that is longer on one side than on the other, or can have any other desired configuration. In addition, the one or more cutting surfaces of the first blade 700 can extend along the entire outer surface of the first blade 700, along a major length of the outer surface (i.e., greater than 50% of a length of the outer surface) of the first blade 700, or along only a minor portion of the outer surface of the first blade 700, such as only at the distal end 705 of the outer surface of the first blade 700.

The second blade 800 of device 500 is similar to the second blade 300 of device 10 and has a cutting surface 815. In some embodiments, the cutting surface 815 of the second blade 800 is less sharp than the cutting surface and/or distal end 705 of the first blade 700. In other cases, the cutting surface 815 of the second blade 800 is sharper than some (or all) of outer surface of the first blade 700. In still yet other cases, the cutting surface 815 of the second blade 800 has the same sharpness as the outer surface (or as the cutting surface) of the first blade 700.

The configuration of the cutting surface 815 of the second blade 800 is also not limited. As shown, the cutting surface 815 can be a curved surface, a straight surface (or uniform length), an angled surface that is longer on one side than on the other side (e.g., a downward-angled cutting surface). In addition, the cutting surface 815 can face toward or away from the handle 600, or can face toward either side of the tissue cutting device 500. In some cases, the cutting surface 815 is provided on an interior surface of the second blade 800. In other cases, the cutting surface 815 is provided on an outer surface of the second blade 800 (e.g., so as to provide a superficial cutting surface). In certain embodiments, the cutting surface 815 of the second blade 800 is a retrograde cutting surface configured to facilitate cutting of tissue when the second blade 800 is moved in a retrograde manner. In other cases, the cutting surface 815 of the second blade 800 is an antegrade cutting surface configured to facilitate cutting of tissue when the second blade 800 is moved in an antegrade manner. Skilled artisans will understand that the examples identified herein are not limiting, and that any type of cutting surface can be used as cutting surface 815.

Although only one cutting surface 815 is shown in the drawings, the second blade 800 can have any desired number of cutting surfaces 815, each having any desired configuration. In some cases, the second blade 800 is provided with a single cutting surface 815. In other cases, the second blade 800 has more than one cutting surface 815 to allow the tissue cutting device 500 to achieve cuts in multiple directions.

Figure 11:
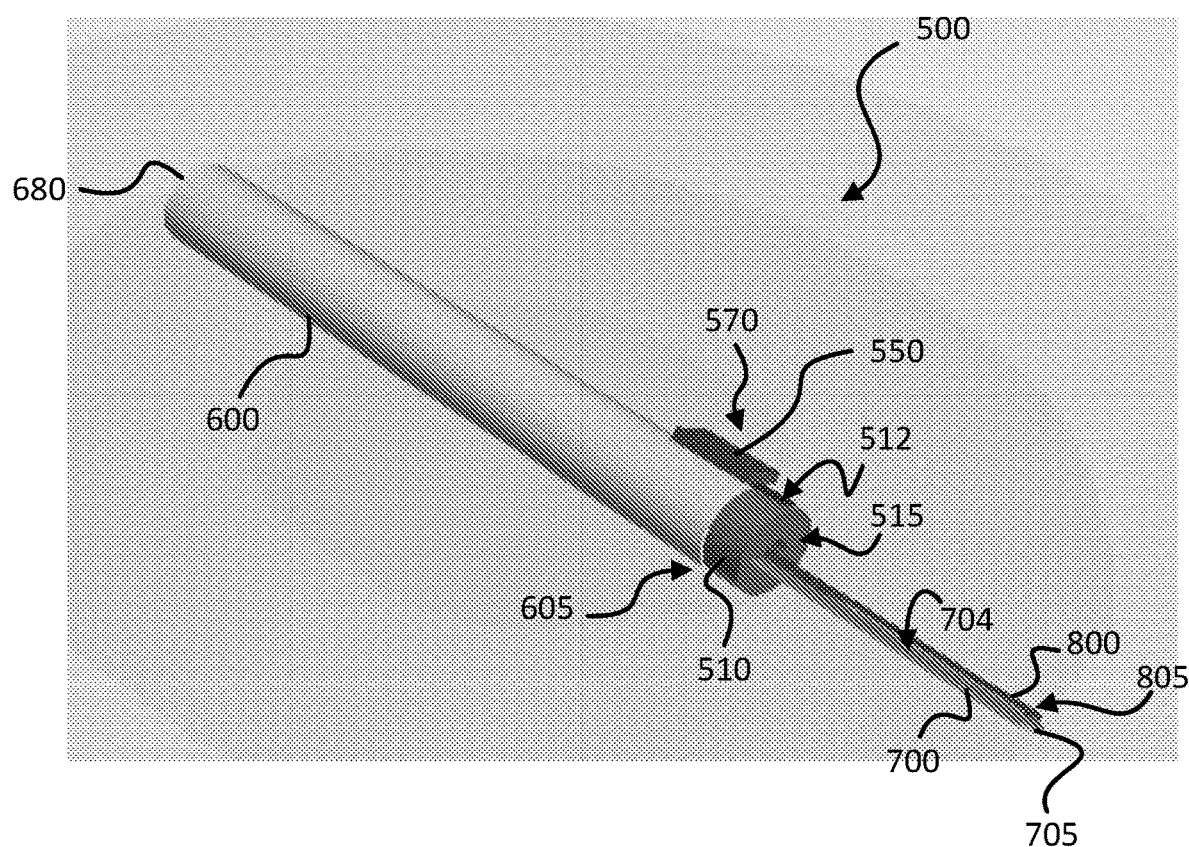
FIG. 11 is a top perspective view of a tissue cutting device in accordance with certain embodiments of the present disclosure, showing a second blade in a first (inactive) position.
Figure 12:
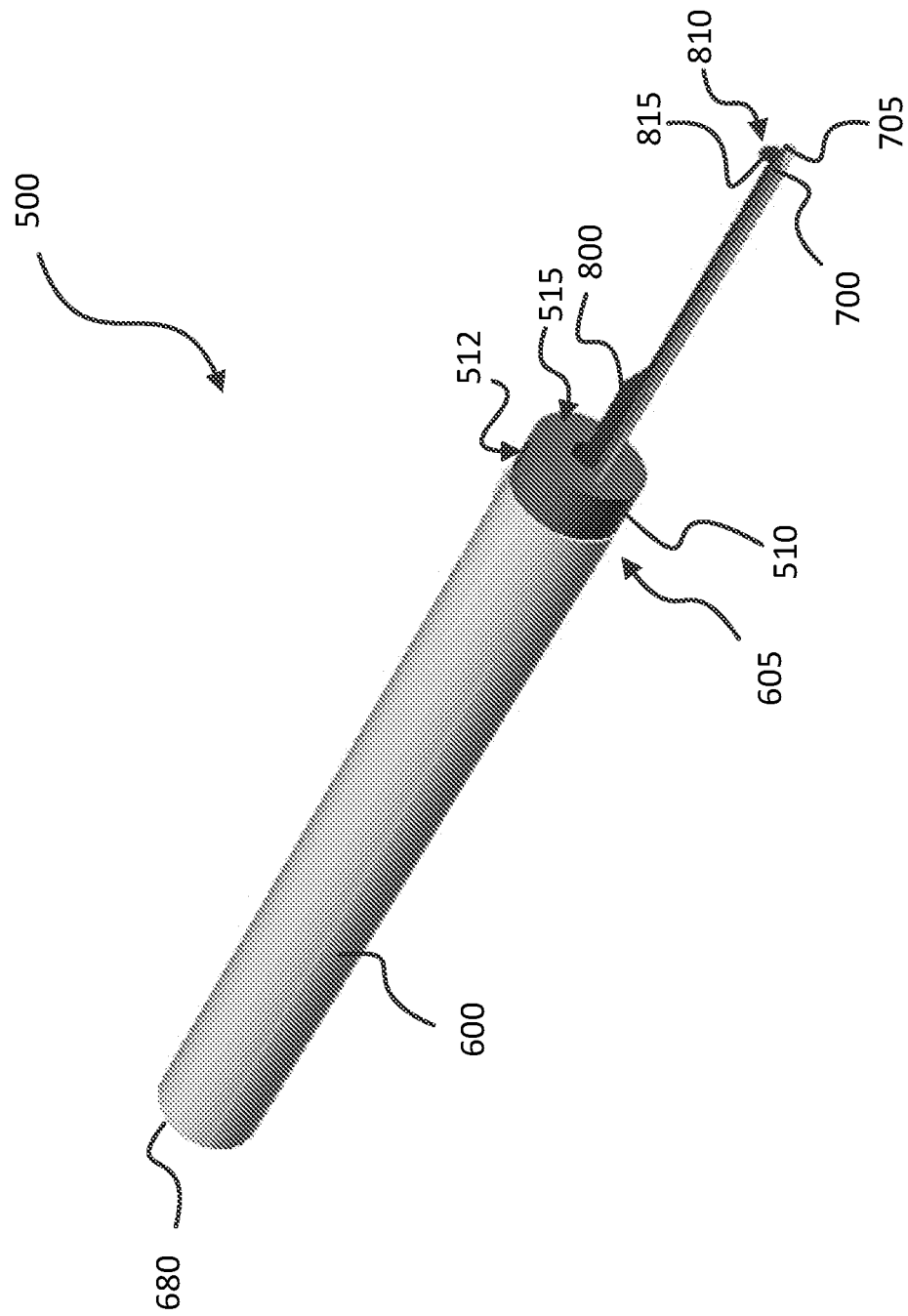
FIG. 12 is a top perspective view of the tissue cutting device of FIG. 11, with both an actuator and a lock of the tissue cutting device removed, and showing the second blade in a second (active) position.
Figure 19:
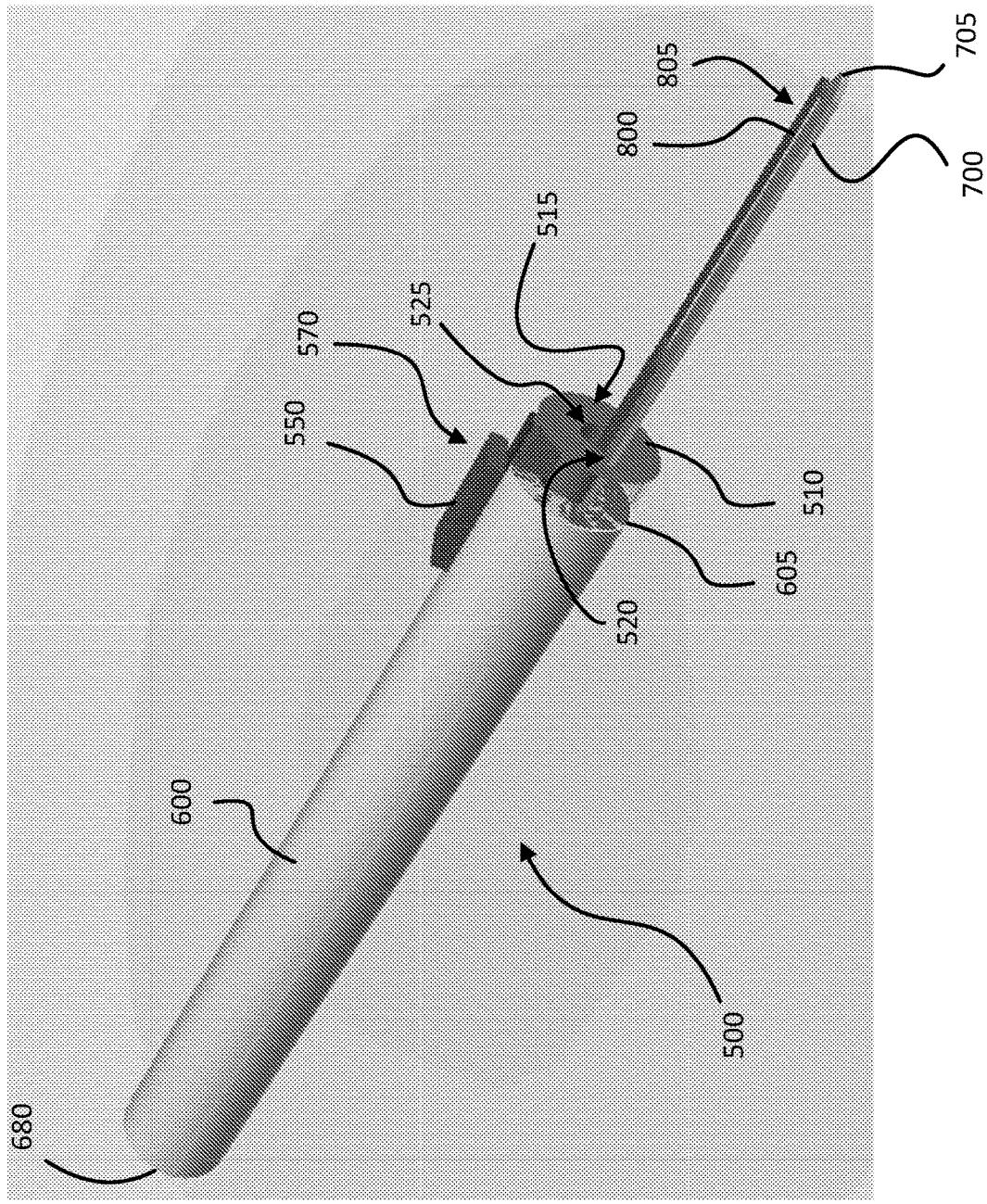
FIG. 19 is a top perspective view of the cutting device of FIG. 11, with a portion of the cover removed and showing the second blade in the first position.
Figure 20:
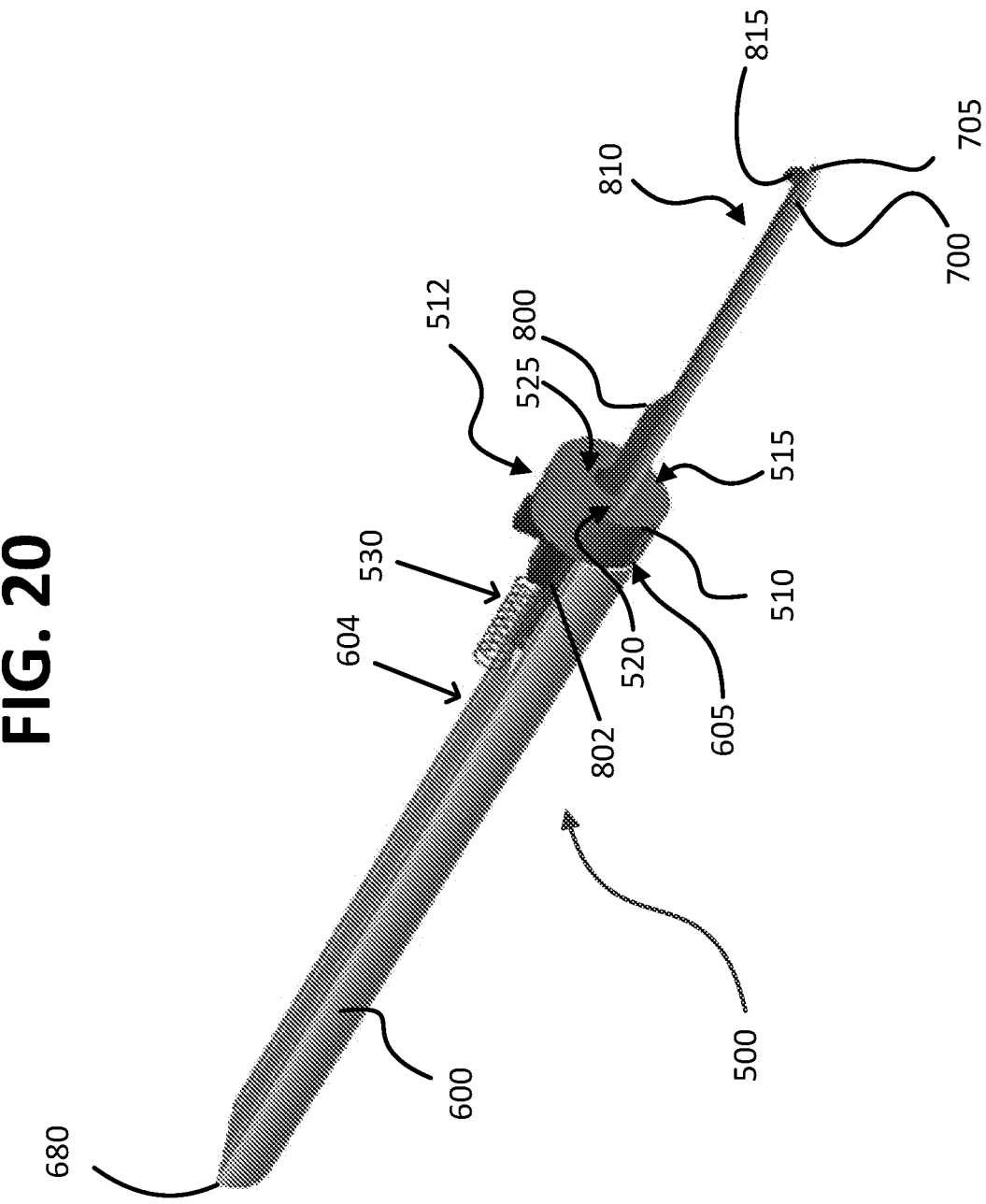
FIG. 20 is a top perspective view of the cutting device of FIG. 11, with a portion of the handle removed, and showing the second blade in the second position.

The second blade 800 is rotatable relative to the first blade 700 such that the second blade 800 is configured to rotate between a first (inactive) position 805 (FIGS. 11, 18, and 19) and a second (active) position 810 (FIGS. 12 and 20). The second blade 800 is in a same plane as the first blade 700 when the second blade 800 is in the first position 805. The second blade 800 is in a different plane from the first blade 700 when the second blade 800 is rotated from the first position 805 toward the second position 810. This can be appreciated by comparing FIG. 11 with FIG. 12.

Figure 18:
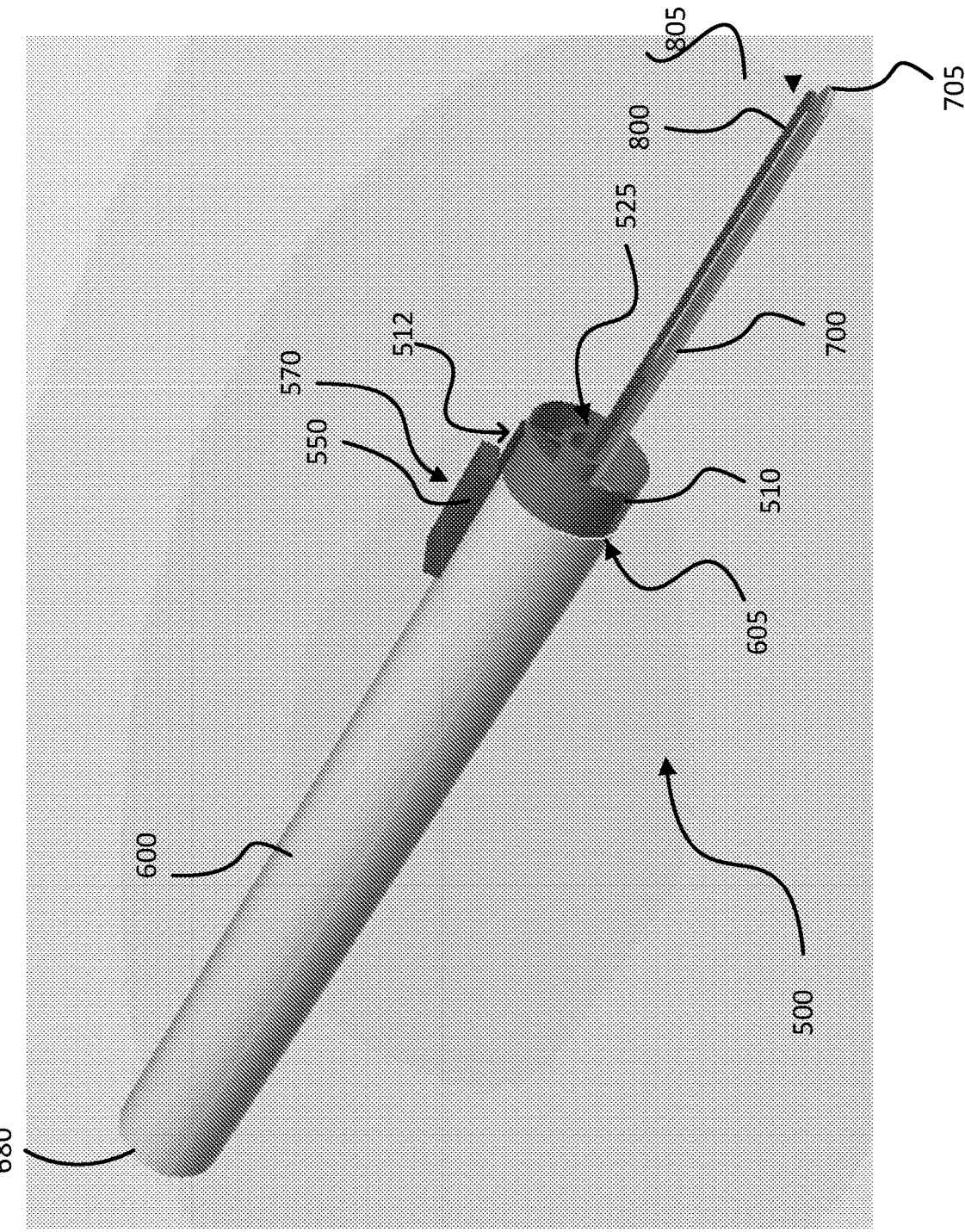
FIG. 18 is a top perspective view of the tissue cutting device of FIG. 11, with a top end of the cover removed, and the second blade in the first position.

FIGS. 11, 18 and 19 show that both the first blade 700 and the second blade 800 lie flat (i.e., parallel or substantially parallel) relative to each other when the second blade 800 is in the first position 805. This arrangement of the tissue cutting device 500 provides a low-profile design that enables the tissue cutting device 500 to be inserted into tight spaces underneath a patient's skin, adjacent a desired tissue region.

The second blade 800 is rotated into a different plane from the first blade 700 as the second blade 800 is rotated from the first position 805 toward the second position 810. As described in greater detail below, when the second blade 800 is in the first (inactive) position 805, the second blade 800 is an unexposed blade that is protected from contacting tissue. The second blade 800 can remain in the first position 805 until needed for a cutting procedure. Then, when it is desired to cut tissue using the second blade 800, the second blade 800 is rotated into the second (active) position 810, thereby becoming an exposed blade.

In preferred embodiments, the first blade 700 is in contact (e.g., direct physical contact) with the second blade 800 when the second blade 800 is in the first position 805. This configuration is shown schematically in FIG. 17B. In some cases, the shaft 702 of the first blade 700 has a recessed area (not shown) in an upper surface 704 thereof configured to receive the shaft 802 of the second blade 800. This arrangement allows the second blade 800 to be recessed into the first blade 700. The depth of the recessed area in the shaft 702 of the first blade 700 is variable such that the extent to which the first blade 700 is recessed into the second blade 800 is also variable. The recessed area in the shaft 702 of the first blade 700 can be an imprint formed in any conventional manner, e.g., by stamping. In certain embodiments, the first blade 700 is entirely recessed within the second blade 800 when the second blade 800 is in the first position 805. In such cases, when the second blade 800 is rotated from the first position 805 toward the second position 810, at least a portion of the second blade 800 rotates out of the recessed area of the first blade 700. In other cases, the shaft 702 of the first blade 700 does not include a recessed area. Instead, the second blade 800 is positioned so as to lie on top of, and directly contact, the upper surface 704 of the first blade 700.

In still yet other cases, the first blade 700 and the second blade 800 are not in direct contact when the second blade 800 is in the first position 805 such that a gap is formed between the first 700 and second 800 blades. However, since tissue may become trapped within the gap, it is preferable that the gap (where present) be as small as possible.

In certain embodiments, the tissue cutting device 500 is hingeless. In such embodiments, as shown in FIGS. 11-20, the material properties and design (including the shape of device 500, as well as the thickness and flexibility of the second blade 800) allow the second blade 800 to intrinsically bend relative to the first blade 700. This optional hingeless feature of device 500 is similar to certain hingeless embodiments of device 10.

In other embodiments, the tissue cutting device 500 includes one or more hinges. Any type of conventional mechanical hinge(s) can be used in tissue cutting device 500 to allow second blade 800 to rotate between its first 805 and second 810 positions. In other cases, the second blade 800 is provided with one or more virtual hinges, such as one or more seams that extend (e.g., longitudinally in series) along a longitudinal axis of the second blade 800. In such instances, the one or more seams extend along the second blade 800 at location(s) where the second blade 800 is materially coupled to the first blade 200 such that the one or more seams are provided at junction(s) of the first blade 700 and the second blade 800. The second blade 800 can be thinner in the region where the one or more seams are located so as to reduce resistance of the second blade 800 to bending. In this manner, the one or more seams facilitate folding and bending of the second blade 800 along the second blade's longitudinal axis for rotating the second blade 800 from its first position 805 toward its second position 810.

The second blade 800 rotates between the first position 805 and the second position 810 in response to rotation of the handle 600. Thus, the second blade 800 and the handle 600 rotate together. The first blade 700 is configured to remain stationary or substantially stationary when the second blade 800 rotates from the first position 805 toward the second position 810. The second blade 800 is configured to rotate along its longitudinal axis when the second blade 800 rotates between the first position 805 and the second position 810.

The second blade 800 can have any desired degree of rotation as needed to suit a particular cutting procedure. In some instances, the second blade 800 is configured to rotate in a range of between 0 and 360 degrees, including any degree therebetween. In other cases, the second blade 800 is configured to rotate in a range of between 0 and 180 degrees, including any degree therebetween. In still other cases, the second blade 800 is configured to rotate in a range of between 0 and 90 degrees, including any degree therebetween. In certain embodiments, the degree of rotation of the second blade 800 can be adjustable. Such adjustability can advantageously help account for anatomic variations between patients.

The handle 600 defines a housing having an interior surface 626. In some cases, the handle 600 comprises a single-piece structure. In other instances, the handle 600 comprises multiple sections, such as a first section 622 and a second section 624 that are coupled (e.g., molded) together. In some embodiments, the interior surface 626 of the handle 600 has a recess 630 formed therein. The recess 630 is sized and shaped such that the recess 630 is configured to receive a shaft 802 of the second blade 800. Where the handle 600 includes the first section 622 and the second section 624, the recess 630 is formed in at least one of the first section 122 and the second section 124 (and in some cases, both sections) of the handle 600. The coupling of the second blade 800 and the handle 600 ensures that the handle 600 and the second blade 800 rotate together.

The handle 600 has an interior 604. In some cases, the interior 604 of the handle 600 includes vertical side walls 606 and a medial wall 608 coupled to and extending horizontally between at least two of the vertical side walls 606. The vertical side walls 606 and the medial wall 608 define a chamber 610 within the interior 604 of the handle 600.

Figure 15:
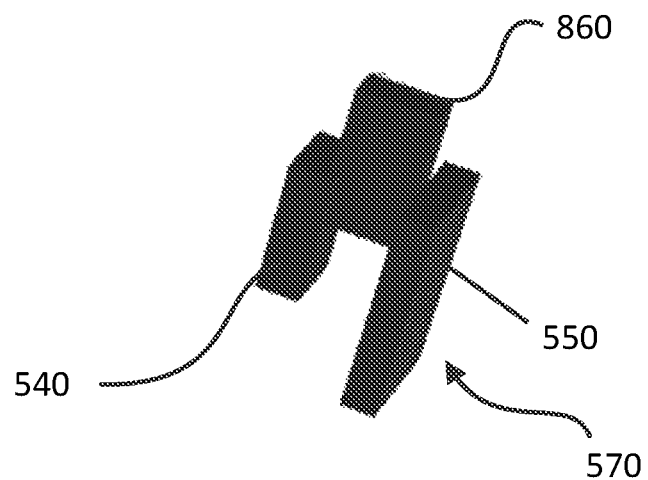
FIG. 15 is a side perspective view of a lock, an actuator, and a projection of a tissue cutting device in accordance with certain embodiments of the present disclosure.
Figure 16:
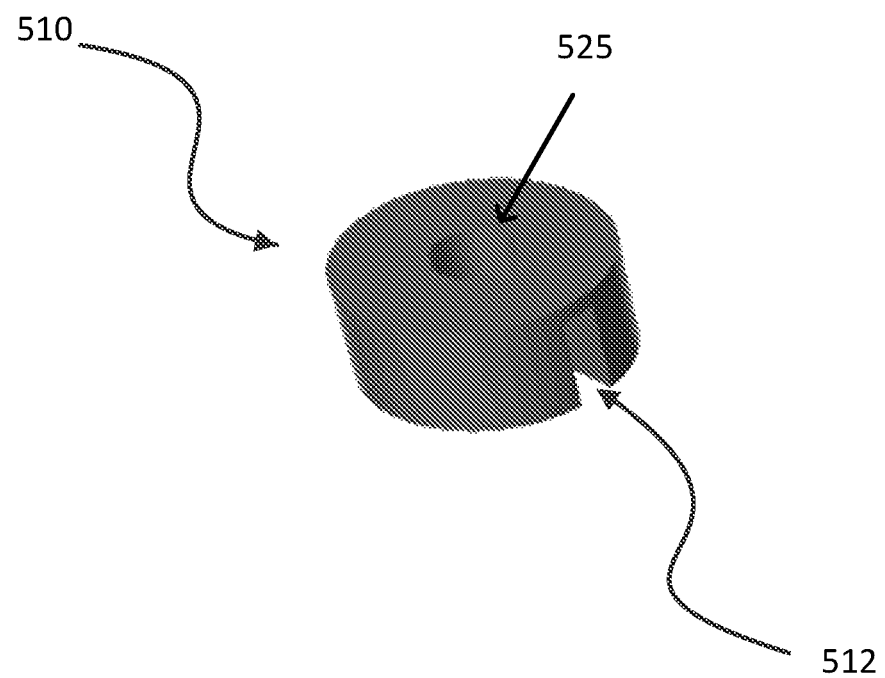
FIG. 16 is a top perspective view of a cover of a tissue cutting device in accordance with certain embodiments of the present disclosure.

In certain embodiments, the tissue cutting device 500 further comprises a lock 860 (FIGS. 13, 14, and 15). The lock 860 has a locked configuration and an unlocked configuration. When the lock 860 is in the unlocked configuration, the second blade 800 is rotatable from the first position 805 toward the second position 810. When the lock 860 is in the locked configuration, the lock 860 is configured to restrain the second blade 800 from rotating relative to the first blade 700. The second blade 800 is locked in the first position 805 when the lock 860 is in the locked configuration.

The tissue cutting device 500 also includes a cover 510. The cover 510 is coupled to an upper end 605 of the handle 600. The handle 600 is rotatable relative to the cover 510 to permit the second blade 800 to rotate from the first position 805 toward the second position 810. In embodiments that include the lock 860, the handle 600 is rotatable relative to the cover 510 when the lock 860 is in the unlocked configuration, whereas the handle 600 is restrained from rotating relative to the cover 510 when the lock 860 is in the locked configuration.

In certain embodiments, the cover 510 has a notch 512 formed therein (e.g., in a side surface thereof). The lock 860 is received in the notch 512 when the lock 860 is in the locked configuration. Then, the lock 860 can be disengaged from the notch 512 when the operator desires to cut a desired tissue. This in turn disengages the cover 510 from the handle 600 and allows the handle 600 to rotate relative to the cover 510. In some cases, the cover 510 and the handle 600 are connected via snap fit notches that allow free rotation of the handle 600 relative to the cover 510 when the lock 860 is in the unlocked configuration.

In certain embodiments (not shown), the cover 510 includes more than one notch 512. The cover 510 can include any desired number of notches 512. Multiple notches 512 allow the operator to control axial rotation of the second blade 800 within a specified range (i.e., between adjacent notches 512) that is dictated by the notches 512. For example, the cover 510 can include four notches 512, each spaced equally apart about a perimeter of the cover 510. In this non-limiting example, by rotating the second blade 800 between one or more adjacently positioned notches 512, the operator is able to lock the second blade 800 in place after rotating the second blade 800 exactly 90 degrees, exactly 180 degrees, exactly 270 degrees, or exactly 360 degrees.

A top end 515 of the cover 510 has both a first opening 520 and a second opening 525 formed therein. The first opening 520 is configured to receive the first blade 700. The second opening 525 is configured to receive the second blade 800. In certain preferred embodiments, the first blade 700 is mounted within a slot defined by the first opening 520. In some cases, the first blade 700 is glued within the slot. This, however, is by no means required. For instance, the first blade 700 can be mounted in the slot of the first opening 520 in any conventional manner.

Figure 17A:
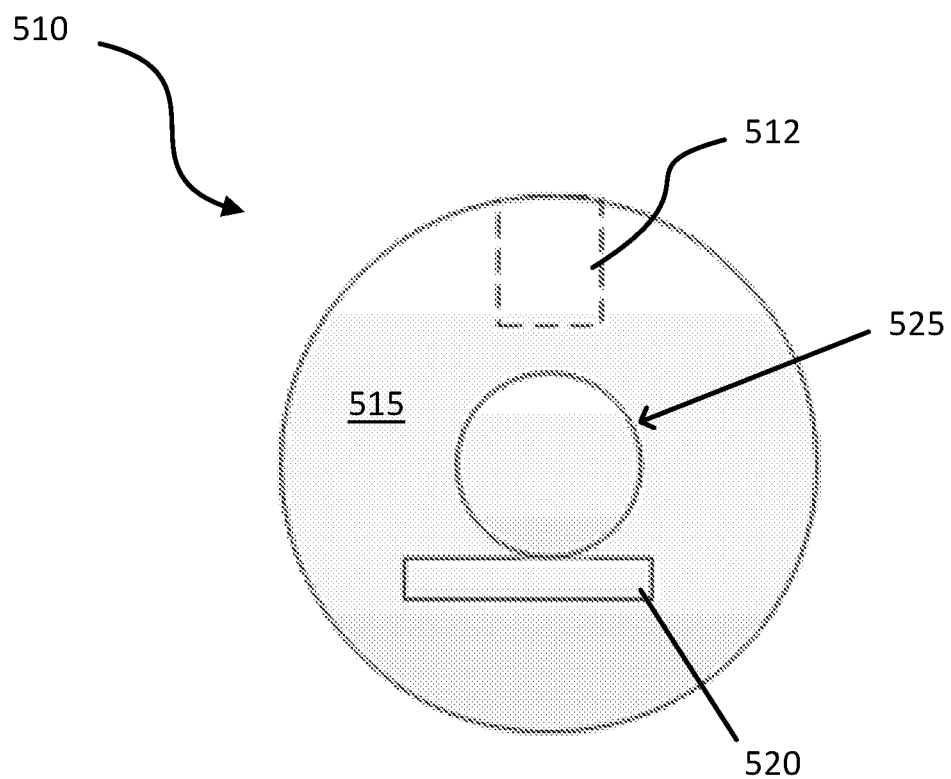
FIG. 17A is a top schematic view of an embodiment of a cover in accordance with certain embodiments of the present disclosure.
Figure 17B:
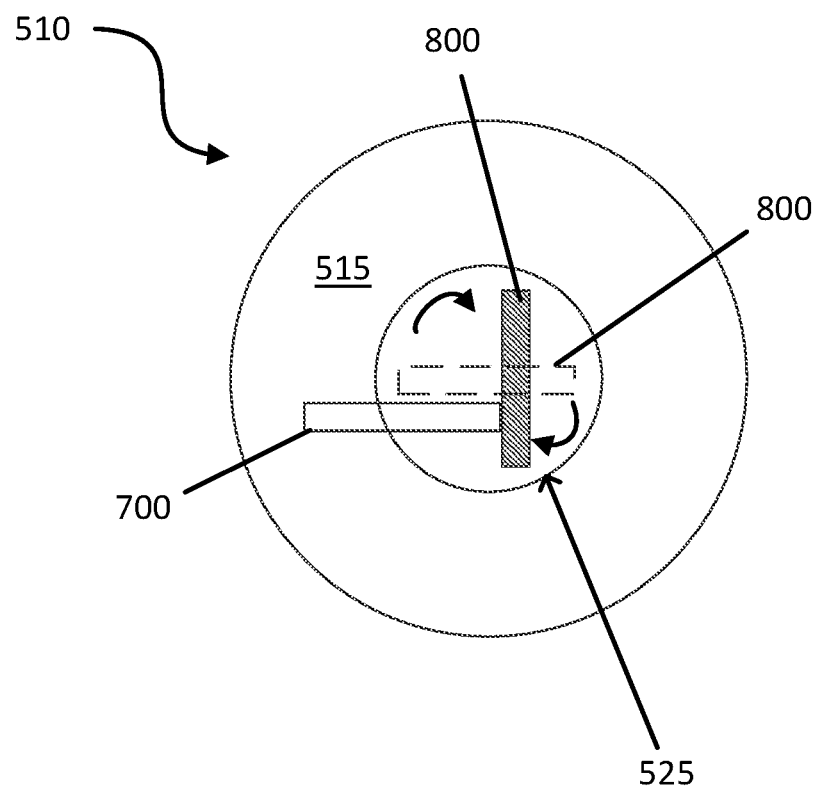
FIG. 17B is a top schematic view of yet another embodiment of a cover, schematically showing rotation of the second blade between the first and second positions, with the second blade resting on the first blade when the second blade is in the first position.

In preferred embodiments, the first opening 520 is laterally offset from the second opening 525 so as to arrange the blades 700, 800 in an L-shaped configuration. This arrangement, which is shown in FIG. 17A, helps prevent the entrapment of tissue, and allows the second blade 800 to rotate without interference from the first blade 700. In other cases, the first opening 520 is centered between opposite sides of the cover 510, such that the first 700 and second 800 blades are arranged in a T-shaped configuration.

The tissue cutting device 500 also includes a biasing member 530. The biasing member 530 is positionable within the interior 604 of the handle 600, particularly within the chamber 610. In certain embodiments, the biasing member 530 is operably coupled to the lock 860 so as to resiliently bias the lock 860 into the locked configuration. In other cases (e.g., in embodiments where there is no lock 860), the biasing member 530 merely biases the handle 600 toward the cover 510. In some embodiments, as shown in FIGS. 13, 14, and 20, the biasing member 530 is a spring.

Certain embodiments of the tissue cutting device 500 further include a projection 540. The projection 540 is attached to the lock 860. The projection 540 is also positionable within the interior 604 of the handle 600, particularly within the chamber 610. When in an uncompressed state, the biasing member 530 is configured to urge against the projection 540 so as to provide upward force to the lock 860 to retain the lock 860 in the locked configuration. The projection 540 is also configured to apply a counterforce to the biasing member 530 (so as to compress the biasing member 530) when the lock 860 is moved from the locked configuration to the unlocked configuration. In preferred cases, the lock 860 (whether in the locked or unlocked configuration) is positioned nearer to the cover 510 than is the projection 540.

In some embodiments, the tissue cutting device 500 includes an actuator 550. The actuator 550 is coupled to the lock 860 and is configured to move the lock 860 between the locked and unlocked configurations. In certain embodiments, the handle 600 has a slot 602 formed in an outer surface 603 thereof. The actuator 550 is slidably mounted in the slot 602 and is movable between a first position and a second position (e.g., using the operator's thumb or other finger). Slidable movement of the actuator 550 between its first and second positions causes the lock 860 to move between its locked and unlocked configurations. In more detail, when the actuator 550 is in the first position, the lock 860 is in the locked configuration. When the actuator 550 is in the second position, the lock 860 is in the unlocked configuration. When the lock 860 is received in the notch 512 of the cover 510, the notch 512 is aligned with the slot 602.

In certain embodiments, the lock 860 is positioned between the projection 540 and the actuator 550. However, in alternative embodiments, the lock 860 and the projection 540 can be vertically aligned with respect to each other and each coupled to the actuator 550.

In certain embodiments, to use tissue cutting device 500, the operator pulls the actuator 550 toward a bottom end 680 of the handle 600 (i.e., a proximal end of the device 500). This in turn causes the lock 860 to be pulled away from (and out of) the notch 512. Thus, the actuator 550 can be pulled to disengage the lock 860, thus allowing the second blade 800 to rotate from the first position 805 toward the second position 810.

An outer surface 570 of the actuator 550 can optionally comprise a material, or include surface features, configured to facilitate gripping of the actuator 550. For instance, in some embodiments, the outer surface 570 of the actuator 550 comprises rubber or another suitable gripping material. In addition or alternatively, the outer surface 570 of the actuator 550 can include surface features, such as textured ridges, to facilitate sliding of the actuator 550 between its first and second positions.

In alternative embodiments, the cover 510 is devoid of an actuator 550 and notches 512, and instead is merely activated by friction. In such cases, the tissue cutting device 500 can include at least one tooth (e.g., a plurality of teeth) or any high-friction surface (e.g., rubber). The teeth or high friction surface of device 500 are configured to restrain the handle 600 from rotating relative to the cover 510 such that the handle 600, when rotated, can be locked into any position along a 360-degree arc about the cover 510. The teeth (or high-friction surface) can be provided on the cover 510, on the handle 600, or on both the handle 600 and the cover 510. Where the teeth (or high-friction surface) are provided on the cover 510, the handle 600 is restrained from rotating relative to the cover 510 when the teeth (or high-friction surface) are in contact with an adjacent surface of the handle 600. Where the teeth (or high-friction surface) are provided on the handle 600, the handle 600 is restrained from rotating relative to the cover 510 when the teeth (or high-friction surface) are in contact with an adjacent surface of the cover 510. In use, the handle 600 is pulled away from the cover 510 to compress the biasing member 530. The handle 600 can then be rotated any desired degree relative to the cover 510 to rotate the second blade 300 any desired degree from the first position 805 toward the second position 810.

The dimensions of tissue cutting device 10, tissue cutting device 500, and tissue cutting device 900 are not limited to the particular dimensions shown, but instead, can have any dimensions needed to suit a particular cutting procedure. For instance, a width and/or length of the first blade 200, 700, the second blade 300, 800, the handle 100, 600, and/or the housing 120 can be varied as desired.

The present disclosure also provides a method of using the cutting devices 10, 500, 900 to cut the soft tissue (e.g., ligament, fascia, or tendon) of a patient. In certain embodiments, the present disclosure provides a method of performing an A1 pulley release procedure to treat trigger finger. However, it should be understood that the present methods can be used to cut any soft tissue structure.

Generally, the method of the present disclosure includes the steps of (a) providing a soft tissue cutting device 10, 500, 900; (b) advancing the tissue cutting device 10, 500, 900 to a body region; (c) rotating the second blade 300, 800 from the first position 305, 805 to the second position 310, 810; and (d) cutting soft tissue in the body region using the second blade 300, 800 when the second blade 300, 800 is in the second position 310, 810. Unless stated otherwise, for any method of the present disclosure, any of tissue cutting devices 10, 500, or 900 can be used. As described below, the step of advancing the tissue cutting device 10, 500, 900 to the body region involves using the first blade 200, 700 to introduce the tissue cutting device 10, 500, 900 into the body region.

In preferred embodiments, the method includes applying anesthetic to the patient's skin. Thereafter, the device 10, 500, 900 is placed through and into the patient's skin adjacent a desired tissue plane. In some cases, the device 10, 500, 900 is placed deep to the desired tissue plane such that the tissue to be cut is positioned above the cutting device 10, 500, 900. However, the exact positioning of the device 10, 500, 900 will depend on the configuration of the first blade 200, 700 and the second blade 300, 800, as well as on the type of cutting procedure to be performed.

For the methods of the present disclosure, a small incision is made in the patient's skin. In some cases, this incision can be made by using the first blade 200, 700 where the outer surface of the first blade 200, 700 includes a cutting blade. In other cases, particularly where the outer surface of the first blade 200, 700 is a blunt end, a separate device (i.e., a device other than device 10, 500, or 900) is used to make the incision.

The first blade 200, 700 is then placed into subcutaneous tissue of the patient such that the outer surface of the first blade 200, 700 is adjacent a desired tissue plane. Preferably, this placement is performed under ultrasound guidance. During the insertion and initial placement of the device 10, 500, 900 into the patient's body, the second blade 300, 800 remains in the first position 305, 805. Then, when it is desired to cut the tissue, the handle 100, 600 can be rotated to cause the second blade 300, 800 to rotate from its first position 305, 805 toward its second position 310, 810 so as to become an exposed blade. A cutting surface 315, 815 of the second blade 300, 800 is then used to cut the tissue in a customary manner. As discussed above, the manner of cutting using the second blade 300, 800 will vary depending on the particular type of cutting surface 315, 815, and its location on the second blade 300, 800. For example, the second blade 300, 800 may need to be pushed or pulled to cut the tissue. Once the tissue is cut, the device 10, 500, 900 is pulled out of the incision to complete the surgical procedure. The device 10, 500, 900 can optionally be discarded after use.

Use of embodiments of the device 900 shown in FIG. 21 may include steps in addition to those noted above. For example, when inserting the device 900, the flanges 425, 430 help prevent the operator from inserting the device 900 too far into the body region. Once the device 900 is positioned, an operator can apply rotational force to the second blade 300 (for example, by rotating the handle 100) to cause the one or more break points 450 to disrupt, thereby separating the first blade 200 from the second blade 300. In certain embodiments, the operator can apply shear force (e.g., by pulling or pushing) the handle 100 to cause the one or more break points 450 to disrupt, thereby separating the first blade 200 from the second blade 300. The first blade 200 and the second blade 300 thereby become separate devices. The operator can then freely move and rotate the second blade 300 to perform cutting. After cutting, the operator can grasp the handle 100 and pull the second blade 300 to remove it from the body region. The first blade 200 can remain in the body until after the second blade 300 is removed. The operator can then grasp the flanges 425, 430 of the first blade 200 with fingers and then pull the first blade 200 to remove it from the body region.

Due to the presence of actuator 550 in certain embodiments of device 500, use of device 500 may include steps in addition to those noted above. In particular, once the positioning of device 500 is confirmed (e.g., under ultrasound), the operator can slide the actuator 550 from the first position to the second position to disengage the lock 860 from the notch 512. The operator then rotates the handle 600 to rotate the second blade 800 from the first position 805 toward the second position 810. Cutting of the tissue of interest (e.g., the A1 pulley) can then be performed by moving the second blade 800 in a conventional manner against the tissue. For embodiments that do not include the actuator 550 or notch(es) 512, the handle 600 is merely pulled away from the cover 510 to compress the biasing member 530, and the handle 600 is then rotated any desired degree relative to the cover 510.

In some cases, the method is an A1 pulley release procedure for treating trigger finger. In such cases, the distal end 205, 705 of the first blade 200, 700 is placed deep to (i.e., below) the A1 pulley and superficial to (i.e., above) the flexor tendon group. The device 10, 500, 900 is initially flat (i.e., parallel to the patient's hand) and placed distal to proximal to the A1 pulley such that the distal end 205, 705 of the first blade 200, 700 faces toward the patient's wrist. In such cases, the device 10, 500, 900 is properly positioned when the first blade 200, 700 is located above the tendon, the second blade 300, 800 is located above the first blade 200, 700 and below the A1 pulley, and the patient's skin is located above the A1 pulley. Thereafter, the handle 100, 600 is rotated so as to rotate the second blade 300, 800 from its first position 305, 805 toward its second position 310, 810. This rotation exposes the second blade 300, 800 to the A1 pulley. The second blade 300, 800 is then used to cut the A1 pulley, for example, by moving the second blade 300, 800 in a retrograde manner (i.e., proximal to distal) against the A1 pulley.

For the above-described methods, and with respect to devices 10 and 900 in particular, upward force from the tendon, as well as a counterforce from the A1 pulley, help keep the second arm 405 parallel to the plane of the A1 pulley while the second blade 300 rotates from the first position 305 to the second position 310.

While tissue cutting devices 10, 500, and 900 have been described as having first and second blades, skilled artisans will appreciate that alternative cutting mechanisms can be used. For example, in some embodiments, the first blade, second blade, or both can be replaced with a cutting mechanism configured to use electricity, heat, radiofrequency, or laser to cut soft tissue. Except for the type of cutting mechanism, such tissue cutting devices are otherwise the same as those that have been described above and can generally be used in a similar manner.

While some preferred embodiments of the invention have been described, it should be understood that various changes, adaptations and modifications may be made therein without departing from the spirit of the invention and the scope of the appended claims.

What is claimed is:

1. A tissue cutting device for performing a trigger finger release procedure, the tissue cutting device comprising:
    a flat handle, comprising;
        a first handle portion; and
        a second handle portion attached to the first handle portion via multiple break points;
    a first blade extending from the first handle portion and comprising:
        a first arm extending from a first proximal end at the first handle portion to a first distal end;
        a second arm extending parallel to the first arm from a second distal end to a second proximal end in a direction of the second handle portion without contacting the second handle portion; and
        a distal tip connecting the first distal end of the first arm with the second distal end of the second arm and including a forward-facing cutting edge; and
    a second blade extending from the second handle portion parallel to and between the first arm and the second arm and including a cutting edge with a hook shape that faces the handle,
    wherein the first arm, the second arm, and the distal tip of the first blade surround at least a majority of the second blade, and
    wherein the second handle portion is rotatable relative to the first handle portion to break the second handle portion from the first handle portion at the multiple break points and rotate the second blade relative to the first blade, such that the second blade rotates from a first plane to a second plane and into a position for cutting a target tissue with the cutting edge.

2. The tissue cutting device of claim 1, wherein the multiple break points attaching the first handle portion to the second handle portion comprise snap perforations.

3. The tissue cutting device of claim 1, further comprising a flange extending from the second proximal end of the second arm of the first blade.

4. The tissue cutting device of claim 3, wherein the flange extends radially outward from the second proximal end of the second arm of the first blade.

5. The tissue cutting device of claim 4, wherein the flange is integral to the first blade.

* * * * *